United States Patent
Allison et al.

(10) Patent No.: US 10,744,140 B2
(45) Date of Patent: *Aug. 18, 2020

(54) SYNERGISTIC NUTRACEUTICAL BEVERAGE FORMULATIONS PROVIDING ENHANCED THERMOGENESIS, MENTAL CLARITY, AND STAMINA WHILE MINIMIZING ADRENALINE AND DOPAMINE CONCENTRATION PERTURBATIONS ASSOCIATED WITH WITHDRAWAL

(71) Applicant: Power Supplements, LLC., Houston, TX (US)

(72) Inventors: Jason Kelly Allison, Houston, TX (US); Guillermo A Amtmann, Houston, TX (US); John Burton Steele, Houston, TX (US)

(73) Assignee: Power Supplements, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/653,869

(22) Filed: Jul. 19, 2017

(65) Prior Publication Data

US 2018/0055850 A1    Mar. 1, 2018

Related U.S. Application Data

(63) Continuation of application No. 15/225,391, filed on Aug. 1, 2016, now abandoned.

(51) Int. Cl.

| | |
|---|---|
| *A61K 31/522* | (2006.01) |
| *A23L 2/52* | (2006.01) |
| *A23L 2/60* | (2006.01) |
| *A23L 2/56* | (2006.01) |
| *A61K 9/00* | (2006.01) |
| *A61K 45/06* | (2006.01) |
| *A61K 36/74* | (2006.01) |
| *A61K 31/135* | (2006.01) |
| *A61K 31/137* | (2006.01) |
| *A23L 2/54* | (2006.01) |

(52) U.S. Cl.
CPC .............. *A61K 31/522* (2013.01); *A23L 2/52* (2013.01); *A23L 2/54* (2013.01); *A23L 2/56* (2013.01); *A23L 2/60* (2013.01); *A61K 9/0095* (2013.01); *A61K 31/135* (2013.01); *A61K 31/137* (2013.01); *A61K 36/74* (2013.01); *A61K 45/06* (2013.01); *A23V 2002/00* (2013.01)

(58) Field of Classification Search
CPC .. A61K 31/522; A61K 9/0095; A61K 31/135; A61K 31/137; A61K 36/74; A61K 45/06; A23L 2/52; A23L 2/54; A23L 2/56; A23L 2/60; A23V 2002/00
See application file for complete search history.

(56) References Cited

U.S. PATENT DOCUMENTS

| | | | |
|---|---|---|---|
| 4,041,074 A * | 8/1977 | Main ................. | C07C 235/12 |
| | | | 562/467 |
| 8,475,851 B2 | 7/2013 | Herrmann et al. | |
| 9,186,350 B2 | 11/2015 | Blackman | |
| 2004/0077556 A1 | 4/2004 | Chinery | |
| 2006/0204599 A1 | 9/2006 | Wheat | |
| 2006/0235000 A1 * | 10/2006 | Dolina ............... | C07D 213/63 |
| | | | 514/217 |
| 2007/0253941 A1 * | 11/2007 | Naidu ................ | A61K 31/12 |
| | | | 424/94.1 |
| 2010/0151023 A1 * | 6/2010 | Beggan ............ | A61K 31/4415 |
| | | | 424/472 |
| 2011/0281808 A1 | 11/2011 | Kichuk et al. | |
| 2012/0177800 A1 * | 7/2012 | Alexander .......... | A23L 29/30 |
| | | | 426/548 |
| 2013/0125904 A1 * | 5/2013 | Chen ................. | A24B 15/24 |
| | | | 131/275 |
| 2014/0107050 A1 * | 4/2014 | Kim ................... | A61K 31/192 |
| | | | 514/27 |
| 2014/0370529 A1 * | 12/2014 | Taverna ............. | G01N 33/6896 |
| | | | 435/7.92 |

OTHER PUBLICATIONS

High Tower Pharmacology: Pharmacology of N-Coumaroyldopamine, Dec. 14, 2011.*
Solinas, Marcello et al., "Caffeine Induces Dopamine and Glutamate Release in the Shell of the Nucleus Accumbens", The Journal of Neuroscience, Aug. 1, 2002, 22(15):6321-6324.
Volkow, ND et al., "Caffeine Increases Striatal Dopamine D2/D3 Receptor Availability in the Human Brain", Translational Psychiatry (2015) 5, e549; doi:10.1038/tp.2015.46, published online Apr. 14, 2015, www.nature.com/tp.
Xie, Z. et al., "B-phenylethylamine Alters Monoanime Transporter Function via Trace Amine-Associated Receptor 1: Implication for Modulatory roles of Trace Amines in Brain". The Journal of Pharmacology and Experimental Therapeutics. vol. 325, No. 2. 617-628, 2008.
Kennedy, D. "B Vitamins and the Brain: Mechanisms, Dose and Efficacy—A Review", Nutrients. Jan. 2016, 8, 68; doi:10.3390/nu8020068. www.mdpi.com/journal/nutrients.

(Continued)

*Primary Examiner* — Blessing M Fubara
(74) *Attorney, Agent, or Firm* — Rao DeBoer Osterrieder, PLLC; Dileep P. Rao

(57) ABSTRACT

The invention describes one or more compositions for causing an increase in thermogenesis in mammals, comprising at least caffeine, hordenine and β-phenylethylamine and optionally the addition of B vitamins. The caffeine is often provided from green coffee bean extracts and normally comprises from 0.0001 g to 0.30 g of caffeine from 0.00001 g to 0.1 g of hordenine from barley and from 0.00001 g to 1.0 g β-phenylethylamine from cocoa beans. The present invention finally provides a method that may cause a simultaneous and synergistic increase in central nervous system activity assisted by the addition of vitamin B as well as thermogenesis in mammals prior to physical exercise, the method comprising providing a composition comprising a source of caffeine, hordenine and β-phenylethylamine.

36 Claims, 9 Drawing Sheets

(56) References Cited

OTHER PUBLICATIONS

Via, Michael, "The Malnutrition of Obesity: Micronutrient Deficiencies That Promote Diabetes". International Scholarly Research Network (ISRN) Endocrinology. vol. 2012, Article ID 103472, 8 pages. doi:10.5402/2012/103472.

Kusaga A., Yamashita Y., Koeda T., Hiratani M., Kaneko M., Yamada S., Matsuishi T. Increased Urine Phenylethylamine after Methylphenidate Treatment in Children with ADHD. Ann Neurol. 2002. 52:372-374.

http://worldofcaffeine.com/caffeine-and-neurotransmitters/. World of Caffeine: The Science and Culture of the World's Most Popular Drug. Accessed Jul. 26, 2016.

Dulloo A.G., Miller D.S. Prevention of genetic fatty acid obesity with an ephedrine-methylxanthines thermogenic mixture. American Journal of Physiology—Regulatory, Integrative, and Comparative Physiology. 1987:252(3 pt 2): R507-513.

Barwell CJ, Basma AN, Lafi MA, Leake LD; Deamination of hordenine by monoamine oxidase and its action on vasa deferentia of the rat; School of Pharmacy, Portsmouth Polytechnic, Hampshire, UK; J Pharm Pharmacol. Jun. 1989;41(6):421-3; PubMed PMID: 2570842.

http://herbpedia.wikidot.com/hordenine.

Hordenine. Wikipedia, the free encyclopedia. https://en.wikipedia.org/wiki/Hordenine. as accessed Jul. 28, 2016.

\* cited by examiner

FIGURE 7A

| RESPONSIBLE PARTY | ACTION STEP |
|---|---|
| Analyst | Measuring Out Solid Ingredients |
| | 1. Weigh out all solid ingredients in the amounts specified by the beverage formulation using clean spatulas/scoops and weighing trays. These include Granulated Sugar (Sucrose), Citric or Malic Acid, Nexex Blend, β-Phenylethylamine (PEA) HCl/Citrate, Hordenine HCl, Stevia, and Beta Carotene 10% (in Citrus). |
| | 2. Combine all of the solid ingredients EXCEPT SUCROSE AND BETA CAROTENE onto one large weighing tray. The beta carotene must be dissolved first followed by the sucrose. |
| | Solubilizing the Solid Ingredients |
| | 3. Measure out 70mL of distilled water for each drink to be produced using a graduated cylinder and transfer it to a 1000mL beaker. (For example, if you are to prepare 6 drinks, measure out 6x70mL=420mL of distilled water) |
| | 4. Add a clean stir bar, transfer the beaker to the stir plate, and set to stir. Add heat (setting 10). Monitor the temperature of the solution using a thermometer. The temperature need not exceed 35°C. |
| | 5. Once the water has come to 35°C, add all of the beta carotene to the beaker and allow todissolve completely. |
| | 6. Once the beta carotene is completely dissolved, carefully and slowly add all of the sucrose. |
| | 7. Allow the solution to stir with heat until all of the sucrose has been dissolved. |
| | 8. Once all of the sucrose has dissolved, turn off the heat and carefully add the remaining solid ingredients. |
| | 9. Allow the solution to stir until all solutes are dissolved and the solution almost completely translucent. |
| | Adding the Liquid Ingredients |
| | 10. Once all of the solid ingredients have been dissolved, measure out the liquid ingredients in the amounts specified by the beverage formulation using a pipette and with clean tips. |
| | 11. Add each liquid ingredient directly to the stirring solution. |
| | 12. Allow solution to stir until it becomes completely clear and no solid particles are observed. |
| | 13. Transfer the concentrated beverage formulation solution to an appropriate sealable container and bring it to the carbonator in the production area. |

| RESPONSIBLE PARTY | ACTION STEP |
|---|---|
| Analyst | Canning and Sealing the Energy Beverage Formulation(s) Drink |
| | 14. Transfer the formulation beverage solution to an appropriately-sized graduated cylinder and record the volume. |
| | 15. Using a calculator, divide the recorded volume by the number of cans to be produced. |
| | 16. Measure out that volume of the formulation beverage solution into each aluminum can to be filled. |
| | 17. Turn on the RO water system, plug in the carbonator and open its carbon dioxide supply following the directions outlined on these pieces of equipment. |
| | 18. Plug in and turn on the Sealer. |
| | 19. Using the "Wonder Bar" gun, dispense carbonated water into each can and fill to the brim. Fill and seal one can at a time to preserve carbonation. |
| | 20. Carefully place a can top onto the can and gently press down. Ensure that the top is even. |
| | 21. Place the can on the Sealer stage, flip the green switch down (the mechanisms will begin spinning). Depress the pedal to raise the can and seal it. |
| | 22. Flip the green switch up to stop the mechanisms from spinning and remove the can. |
| | 23. Repeat the Filling and Sealing Procedure until all Energy Drinks are prepared. |
| | 24. Close the valves on the $CO_2$ tank, unplug all equipment, and switch off the RO water supply. |

| Energy Drink – Berry Ingredients | Amt per 355mL can (g) | Amt per 355mL can (mg) | Amt per 355mL can (mL) | Type and Indication or Purpose |
|---|---|---|---|---|
| Filtered Water | N/A | N/A | 329.19 | RO (Reverse Osmosis) water - milliohm rating (DI), municipal, distilled - doubly distilled, filtered |
| Nexex Blend | 0.43 | 425 | N/A | A blend of biotin, B vitamins, caffeine and maltodextrin |
| Hordenine HCl | 0.03 | 33 | N/A | Natural MAO-B inhibitor -blocking to extend half-life of β-phenylethylamine |
| β-Phenylethylamine | 0.31 | 314 | N/A | Decreases uptake of dopamine and norepinephrine and serotonin - energy improves due to thermogenesis - movement and focus improved |
| Malic Acid | 1.00 | 998 | N/A | Flavor enhancer and acidification |
| Granulated Sugar | 36.95 | 36949 | N/A | source of sugar - cane sugar *(displaces 24.26 ml of fluid in beverage- thereby ensuring 355 ml total)* |
| Strawberry Jam Natural Flavor WONF | N/A | N/A | 0.54 | Allen Flavors (in Edison NJ) *WONF (With other natural flavors)* |
| Natural Bitterness Blocker | N/A | N/A | 0.18 | Allen flavors provides |
| Natural Flavor Enhancer Juicy Type | N/A | N/A | 0.24 | Allen flavors provides |
| Masker for Caffeine Natural | N/A | N/A | 0.43 | Allen flavors provides |
| EXBERRY Shade Red | N/A | N/A | 0.14 | Natural coloring |
| Stevia Leaf Extract | 0.03 | 30 | N/A | Artificial sweetening |
| TOTAL | 38.75 | 38749 | 330.72 | |

FIGURE 9

| Energy Drink — ORANGE | Amt per 355mL can (g) | Amt per 355mL can (mg) | Amt per 355mL can (mL) |
|---|---|---|---|
| Filtered Water (water type varies) | N/A | N/A | 329.19 |
| Nexex Blend | 0.43 | 425 | N/A |
| Hordenine HCl | 0.03 | 33 | N/A |
| β-Phenylethylamine | 0.31 | 314 | N/A |
| Citric Acid | 0.92 | 923 | N/A |
| Granulated Sugar (displaces 24.26 ml thereby ensuring 355 ml total) | 41.70 | 41705 | N/A |
| Natural Orange Flavor | N/A | N/A | 0.81 |
| Natural Bitterness Blocker | N/A | N/A | 0.18 |
| Natural Flavor Enhancer Juicy Type | N/A | N/A | 0.08 |
| Masker for Caffeine Natural | N/A | N/A | 0.36 |
| Orange Crush Flavor | N/A | N/A | 0.12 |
| 10% Beta-Carotene CWS | 0.01 | 8 | N/A |
| Stevia Leaf Extract | 0.03 | 33 | N/A |
| TOTAL | 43.44 | 43441 | 330.74 |

FIGURE 10

| Energy (Shot) | Amount (milligrams) |
|---|---|
| Phenylethylamine (PEA) | 300 |
| Hordenine HCL | 30 |
| Caffeine Anhydrous | 150 |
| Total Volume (water solubilizes the three components) | 60mL |

SYNERGISTIC NUTRACEUTICAL BEVERAGE FORMULATIONS PROVIDING ENHANCED THERMOGENESIS, MENTAL CLARITY, AND STAMINA WHILE MINIMIZING ADRENALINE AND DOPAMINE CONCENTRATION PERTURBATIONS ASSOCIATED WITH WITHDRAWAL

PRIORITY

This application is a Continuation of and claims priority under 35 USC 120 of U.S. application Ser. No. 15/225,391 filed Aug. 1, 2016, entitled "SYNERGISTIC NUTRACEUTICAL BEVERAGE FORMULATIONS PROVIDING ENHANCED THERMOGENESIS, MENTAL CLARITY, AND STAMINA WHILE MINIMIZING ADRENALINE AND DOPAMINE CONCENTRATION PERTURBATIONS ASSOCIATED WITH WITHDRAWAL". The entire contents of the application are hereby incorporated by reference.

FIELD OF INVENTION

The present disclosure relates to nutritional and nutraceutical products, particularly to formulations for beverages providing nutritional components that improve both physical and mental aspects of the human condition via thermogenesis. More specifically, the beverage components in this disclosure are designed to boost energy through thermogenesis enhancing compounds as well as increasing mental concentration and stamina while also (and in some cases) simultaneously reducing or eliminating perturbations existing during adrenaline and dopamine withdrawal. Perturbations are defined as rapid changes in concentration levels over relatively short time periods. In this case short time periods for human consumption are normally less than 5-6 hours.

BACKGROUND

A nutraceutical is a food or food product that provides health and medical benefits, including the prevention, treatment, and enhancement of the human condition and in many cases, for the benefit of mammals in general. Most vitamins are made from "food grade" chemicals but a nutraceutical is generally made from pharmaceutical grade chemicals of higher purity and with more predictable and consistent results. Thermogenesis is a term which literally means "the creation of heat". Often, the term thermogenesis is used as a synonym for the term "energy". Energy is transformed, converted, transported, and stored within the human body. Human energy comes into the body from what is normally consumed in the form of food and/or beverage. In many cases, beverages contain food-based substituents including vitamins, minerals, and additional supplements which are contained in many of the foods we consume. One unit of the measurement of heat energy involves the use of the terms "joules or kilocalories" and often kilocalories are counted on food and beverage labels in terms of "calories". Specifically, a calorie is the amount of heat needed to heat one gram of water one degree Celsius. Calories are the unit of measurement describing how much energy is stored in a food or beverage. Water does not contain any calories, however it is normally found in the food and beverages consumed by humans, and as we consume these substances, energy is either transformed or stored. As energy is transported through the body's system, some energy leaves the body as fecal energy. Other energy is lost through the urinary tract. Energy not lost through waste by these two means is available for ensuring at least baseline (or basal) metabolic functions. One of the largest energy expenditures in the human body is thermic (heat) energy. Thermic energy differentiates an endoderm (mammal) from an ectoderm (reptile). The endoderm's basal metabolism is 8 to 10 times higher than that of most ectoderms. Therefore, mammals, and in particular humans, utilize tremendous amounts of the energy that is converted into thermic energy. Energy not used for thermic energy is then available as net energy for the body's cellular reproduction, growth (especially in children), work (muscle movement), and storage. The most common storage form of thermic energy is known as fat.

There are at least three forms of thermogenesis. The first form is work-induced from exercise. It is necessary for human muscles to create or utilize heat in order to work more effectively than when the muscles are cold.

A second form of thermogenesis is known as thermoregulatory thermogenesis. This form provides for keeping the temperature of the human body regulated. The average body temperature is 98.7 degrees (F.). In addition, there are two types of thermo-regulatory thermogenesis: shivering and non-shivering. Shivering helps the body create heat. The skeletal muscles create the shivering. There's a small amount of muscle on each hair that can regulate heat gain and loss.

Non-shivering thermogenesis fits the third classification form, which is also known as diet-induced thermogenesis. Eating a meal or drinking other than water, will produce diet-induced thermogenesis. Normally, humans require more energy to digest food and/or beverages than are being consumed. There are regions within the body that can measure the most critical phenomena regarding the purpose of this disclosure; namely non-shivering or diet-induced thermogenesis.

Diet-induced thermogenesis is very important in animals that hibernate, such as bears, or small animals with a very large surface area in comparison with their body weight. Brown adipose or "brown fat" tissue is where a significant amount of the energy is stored in the body. "Brown fat" is also very prevalent in newborn babies as they exhibit tremendous amounts of non-shivering thermogenesis to regulate their body temperature. As humans age, this system depletes somewhat but remains an important part of survival.

Brown fat (adipose tissue) is located around blood vessels and major organs. When it is actively triggered, it causes the warming of the blood. Warm blood is circulated throughout the body to spread this energy in the form of heat for warming the entire body. The body's thermogenic system triggers the sympathetic nervous system. Under conditions of cold or when larger portions of calories are consumed, the hypothalamus gland registers this energy consumption and then triggers the sympathetic nervous system (also known as an automatic nervous system). The sympathetic nervous system controls many vital functions including heartrate, blood pressure (the circulatory system) and breathing (the respiratory system). Thus, the autonomic (involuntary) nervous system continuously requires and consumes energy.

In the area of the body where the nerves transmit biochemical signals via pathways, one of these neuro "transmitters" is known as norepinephrine. The triggering of the sympathetic nervous system causes the release of norepinephrine from a nerve terminal across the synapse which subsequently binds to receptors to propagate a nerve impulse.

This process increases (in some cases rapidly and dramatically) thermogenesis as well as other activity related functions generated by the nervous system. One way to visualize these somatic (body) functions, is by likening it to raising the body's thermostat. All humans have a basal metabolism rate which can be measured and indicates (in a rather precise manner), the energy required for maintaining vital functions. It is possible, by using formulations described in the present disclosure, to modulate or raise the metabolism rate above the basal rate.

Sweating or perspiration is often associated with one symptom of this increase in thermogenesis. Sweating occurs when more energy is used during thermogenesis of the sympathetic system than the energy used for work related activities. In the case of sweating, less energy is stored and less energy is converted to fat as opposed to when the body is operating at its basal metabolic rate. In this case, less brown fat is activated, thereby further reducing the metabolism of white fat cells, which are the primary fat storage depository in the human body. It is worth noting that although humans have a consistent number of fat cells, the size can greatly vary. The number of fat cells remains the same, but the size changes.

The brown fat cell is unique in its mitochondrion. Mitochondria are the "energy factories"—oxidative phosphorylation sites—for fueling the body. In the brown fat cell, unique mitochondria help create energy. The brown fat cell is also an energy consumer and it is heat energy that is being consumed. It has been postulated that much of human obesity is less associated with eating habits than it is with brown fat cell deterioration. If these cells deteriorate, energy use and release can be severely compromised. Brown fat activity studies are underway which indicate that post-obese people have a deficiency in their brown fat system.

Another symptom of thermogenesis is a loss of appetite. Exercise also increases the metabolic rate above the basal level giving the feeling of more energy due to the fact that more energy has been transported to the red and white blood cells responsible for (among numerous additional functions) oxygen transport and waste removal.

When an intentionally induced form of thermogenesis is created, by for example, the use of nutritional or nutraceutical supplementation with food or beverages, people feel they have more energy. Often they are generally able to perform more work related operations (both physical and mental), which also leads to an increased utilization of fat as the stored calories are converted into released calories. When calories released from the body exceed those consumed, body weight is reduced.

In the past, many of the types of formulations that were designed to provide thermogenesis leading to increased and improved mental stimulation and stamina have also provided deleterious side effects or "symptoms". The beverages of this disclosure have been carefully and precisely formulated to reduce and in some cases completely eliminate these deleterious, unwanted side effects or symptoms.

SUMMARY

Generally, the present disclosure describes synergistic nutraceutical beverage formulations providing enhanced thermogenesis leading to enhanced/improved mental concentration and stamina while minimizing adrenaline and dopamine withdrawal. In most cases these synergistic effects are simultaneous within the consumer's body and are primarily due to the ability to slow the metabolic rate of caffeine and β-phenylethylamine withdrawal when combined with the MAO-B inhibitor, hordenine HCL. It is also clear that combining caffeine, β-PEA, and hordenine (likely) results in a synergistic residual reduction in the withdrawal symptoms associated with catecholamine withdrawal following consumption of the beverage formulation(s) due to the increased half-life of β-PEA. These symptoms are more fully described below. In order to extend physical and mental stamina via thermogenesis and (in some cases) simultaneously reduce unwanted withdrawal symptoms, the present disclosure describes a beverage combination of caffeine, hordenine, and β-phenylethylamine (β-PEA) in specific doses together with a B-vitamin "complex" and water with sugars or sugar substitutes (inactives). This beverage provides not only an increase in thermogenesis associated with a feeling of increased energy due to increased physical metabolic activity, but also stimulates and enhances brain function related to mood and focus. The word "complex" in this case refers to the use of one or more of the B vitamins as listed below, but should not be construed as being a specific combination of B vitamins that has been complexed in any particular combination prior to providing the beverage of the present disclosure.

The vitamin B portion of the beverage is also a composition that comprises, in any combination, some of the water soluble B vitamins, specifically; $B_3$ (Niacinamide) and/or $B_6$ (pyroxidine hydrochloride), $B_9$, folate (folic acid), $B_{12}$ (cyanocobalamin), $B_7$ (biotin) and $B_5$ (pantothenic acid). Vitamin $B_3$ can be present in amounts ranging from about 0.002 g to 0.20 g, vitamin $B_5$ as pantothenic acid is present in the ranges from 0.000001 g to 0.100 g, vitamin $B_6$ can be present in amounts ranging from 0.0002 g to 0.20 g, vitamin $B_7$, in the form of Biotin can be present in the amounts ranging from 0.00001 g to 0.01 g, and vitamin $B_{12}$ can be present in amounts ranging from around 0.000001 g to 0.50 g. Furthermore, vitamin $B_{12}$ can be dosed as cyanocobalamin (a form that the body readily converts to the active forms methylcobalamin and 5-deoxyadenosylcobalamin). Cyanocobolamin can be converted into methylcobolamin and adenosylcobolamin which can be present in amounts ranging from around 0.000001 g to 0.50 g.

One standard 12 oz canned beverage of the present disclosure typically comprises between 50 and 250 calories including between 10 and 50 g total carbohydrates which may include between 10 and 50 g of one or more forms of sugars or sugar substitutes.

In a further embodiment, it was necessary to modify the 12 ounce (or 16 ounce) beverage formulation in order to pass required (aluminum can) corrosivity testing. This was accomplished by substituting 50% of the β-phenylethylamine HCl with β-phenylethylamine citrate thereby changing the pH and corrosive nature of the beverage in its completed form. This modification reduced the chloride concentration significantly allowing for approval for a can warranty.

A one ounce "shot" of the same beverage may be more highly concentrated with respect to caffeine, hordenine, β-PEA and may or may not include the B vitamins, in that this product normally would provide these "active" ingredients dispersed in much less water. Here the term "active" or "actives" is meant to convey the meaning of ingredients that are known to provide active stimulation of thermogenesis and/or brain activity when ingested by humans. Alternatively, the term "inactive" or "inactives" refer to, for example, a simple carrier or binding agent, such as water or primarily inert fillers such as calcium, magnesium, or sodium salts, thickening agents, emulsifying agents, and buffering agents.

In one embodiment, these beverage formulations utilize only components and compounds extracted or derived from earth grown or naturally occurring earth-available substances.

In another embodiment, the composition will optionally contain calcium and magnesium salts. Calcium and magnesium salts can be present in amounts ranging from about 0.001 g to 0.50 g, In a further embodiment, it was necessary to modify the 12 ounce (or 16 ounce) beverage formulation in order to pass required (aluminum can) corrosivity testing. One method to accomplish this requirement was by substituting 50% of the β-phenylethylamine HCl with β-phenylethylamine citrate thereby changing at least the pH and corrosive nature of the beverage in its completed form. This modification reduced the chloride concentration significantly allowing for approval for a can warranty so that the carbonated form of the beverage can be distributed.

More specifically, the present disclosure describes one or more nutraceutical beverage formulations providing enhanced thermogenesis, mental concentration, and stamina to mammals, comprising at least three distinct synergistic components including caffeine, β-phenylethylamine, and hordenine, wherein at least these three distinct components are combined with water and wherein the formulations reduce or eliminate undesirable side effects during or after mammalian ingestion of the beverage formulations.

For these beverage formulations mammals are humans wherein hordenine is hordenine HCl.

In another embodiment the beverage formulations comprise β-phenylethylamine that is either β-phenylethylamine citrate or β-phenylethylamine HCl or a combination of both.

In another embodiment, the synergistic components act to increase catecholamine and indoleamine concentrations and the synergism is accomplished as the catecholamine and indoleamine concentrations cross a blood-brain barrier after consumption, thereby reducing or eliminating acute symptoms associated with rapid decline of the catecholamine and indoleamine concentrations in the blood.

In another embodiment, these synergistic components undergo a metabolic breakdown resulting in a controlled decrease in the catecholamine and indoleamine concentrations such that the concentrations revert to a pre-existing basal level associated with the consumer of the beverage formulation.

These synergistic components provide synergy in that β-phenylethylamine decreases serotonin reuptake, hordenine prevents metabolic breakdown of β-phenylethylamine and maintains serotonin levels, while caffeine decreases serotonin levels.

The synergistic component, β-phenylethylamine corrects for reduction of serotonin levels that occur following prolonged consumption of caffeine.

In another embodiment, three distinct synergistic components are further combined with one or more B vitamins such that these B vitamins provide additional cognitive enhancing attributes to mental clarity, concentration and stamina. More specifically, the three distinct synergistic components are combined with a B vitamin complex, such that the vitamin B complex includes B3, B5, B6, B7, B9, and B12 mixed together in any combination and at any concentration that will further reduce or eliminate side effects associated with any of the three distinct components and the vitamin B complex during or after human ingestion.

In addition, the three distinct synergistic components and one or more B vitamins are further combined with one or more sweeteners including sugars and/or a sugar substitutes.

In an additional embodiment, the beverage formulations include an addition of flavors.

These flavors are natural flavors and can also be organic flavors.

In another embodiment, the caffeine used for these beverages is a green coffee bean extract.

In yet another embodiment, the water is distilled water, deionized water, buffered water, filtered water or any combination thereof. In this case, the buffered water is pH adjusted with buffering agents to either increase or decrease pH of the distilled, deionized, and/or filtered water.

In another embodiment, the beverage formulations include sugars selected from the group consisting of; sucrose, crystalline fructose, high fructose syrups, mannose, dextrose, monk fruit sugar, maple syrup, and honey.

The sugar substitutes are selected from the group consisting of; stevia, saccharin, aspartame and sucralose. In the case of stevia it is an earth grown derived form of stevia, such as from the stevia leaf.

In a further embodiment, these beverage formulations also contain pharmaceutical grade salts selected from the group consisting of calcium salts, magnesium salts, and sodium salts further enhancing the effects associated with these formulations and combinations thereof. Acceptable salts enhance flavor and efficacy of these formulations specific to improving mental clarity, concentration, and both physical and mental stamina.

An important aspect of the present disclosure and associated beverage formulations includes the fact that the water used to produce these beverage formulations is carbonated water. It is also possible to produce these formulations without carbonation.

In a separate embodiment, one or more nutraceutical beverage formulations providing enhanced thermogenesis, mental concentration, and stamina to mammals, comprising at least three distinct synergistic components including caffeine, β-phenylethylamine, and hordenine, provide a boost of energy-generating catecholamines from the caffeine including dopamine and norepinephrine which produces amphetamine stimulation and performance enhancement. In this case, the β-PEA further promotes an efflux of catecholamines which blocks a re-uptake and simultaneously decreases reuptake of serotonin. This decrease may or may not be simultaneous depending on several factors including the consumer's metabolism, concentration of the synergistic components consumed, and the activity before, during and after the consumer has consumed these beverage formulations.

In addition, the hordenine stabilizes the β-PEA in that the β-PEA remains in its pre-consumed form for an extended length of time, normally several hours. Without the addition of hordenine the β-PEA would destabilize and become metabolically consumed much more rapidly.

The β-PEA is a stronger NDRI (Norepinephrine-Dopamine Reuptake Inhibitor) and is a weaker-acting SSRI (Selective Serotonin Reuptake Inhibitor) in terms of providing this type of activity across the blood-brain barrier when consumed by the consumer.

The synergistic action of β-PEA with hordenine and caffeine provide prolonged mental and physical benefits and diminish or eliminate unwanted withdrawal symptoms after consumption by reduction of adrenaline and dopamine perturbations.

In developing these beverage formulations, it has been determined that there are several methods associated with making one or more nutraceutical beverage formulations for increasing thermogenesis. One such method comprises providing at least three distinct synergistic components including caffeine, β-phenylethylamine, and hordenine, and water, such that the components are provided by adding to a container each of the components in selected amounts providing specific concentration(s) and mixing these components into water thereby creating solubility of the components into a solution forming a basis for the formulations.

Additionally, components including sugar, sugar substitutes, B vitamins, colorants and flavorings can be added to the beverage formulations thereby achieving final beverage formulation compositions for mammalian consumption.

These final beverage formulation compositions are used to improve functional conditions in mammals associated with mental clarity, concentration, and stamina.

In a further embodiment, the mammals are humans.

Consumption of these nutraceutical beverage formulations includes an administration route selected from the group consisting of oral buccal, sublingual, and combinations thereof.

The beverage compositions using these methods provides liquid beverages that utilize carbonated water and in some instances, the liquid beverages utilize non-carbonated water.

Most specifically, this disclosure provides for one or more compositions that cause an increase in thermogenesis in mammals, comprising at least caffeine, hordenine and β-phenylethylamine and optionally the addition of B vitamins. The caffeine is often sourced from green coffee bean extracts and normally comprises from 0.0001 g to 0.30 g of caffeine from 0.00001 g to 0.1 g of hordenine sourced from barley and from 0.00001 g to 1.0 g β-phenylethylamine sourced from cocoa beans.

BRIEF DESCRIPTION OF THE DRAWINGS

FIG. 7A and FIG. 7B depict a standard operating procedure (SOP) for making beverages of the present disclosure.

FIG. 8 depicts an energy beverage formulation of the present disclosure.

FIG. 9 depicts another example of the components of a beverage formulation of the present disclosure.

FIG. 10 depicts a third example of the components of a beverage formulation of the present disclosure.

DESCRIPTION

The synergistic beverage formulations providing enhanced thermogenesis together with enhanced mental concentration and stamina and reduced withdrawal (or undesirable physical affects) symptoms contain at least four distinct components. These components include caffeine, hordenine, β-phenylethylamine, and optionally as many as six of the eight known B vitamins, all of which are mixed with deionized, distilled, or otherwise filtered water in a prescribed amount. The beverage composition for the shot form of the beverage may or may not include any of the B-vitamins.

Each of these components have been carefully chosen so that their enhanced synergistic effects can be combined and regulated to ensure a decrease or elimination of undesirable side effects associated with each of these "active" substances.

The simultaneous or combined use of β-phenylethylamine (endogenous in the brain—crosses the blood-brain barrier) and hordenine, where hordenine is provided as an MAO-B inhibitor that prevents the rapid peripheral metabolism-breakdown of β PEA. However, since hordenine is a MAO-B inhibitor it can also prevent the metabolism of dopamine, norepinephrine, and epinephrine as well. The result provides for relative stability of the norepinephrine levels that reach the brain, thereby reducing the possibility of a rapid change resulting in undesirable withdrawal symptoms. Adding B vitamins to support healthy brain and associated nerve function and caffeine to assist with both uptake and release of neurotransmitters, the present disclosure describes a beverage formulation that enhances many aspects of mental concentration and stamina.

In order to fully comprehend the ingenuity associated with these beverage formulations, each of the three distinct components (four if B vitamins are included) and how they interact with each other to enhance physical and mental aspects of the human condition by also lessening or eliminating undesirable side effects, are described in careful detail below.

Caffeine

For the beverages described in this disclosure, the caffeine is derived primarily from green coffee bean extract. It is also possible to provide synthetic caffeine. As with all psychoactive drugs, caffeine achieves its effects by imitating or altering the release or uptake of neurotransmitters, the chemical messengers that direct how the neurons of the CNS (central nervous system) interact with each other. Neurotransmitters are altered by drugs in a variety of ways, including increasing or decreasing their synthesis, inhibiting or enhancing their transport, modifying their storage, release, or the way they are degraded, or simply by directly mimicking their activity or, alternatively, by blocking their action at the receptor site.

Figure 1:
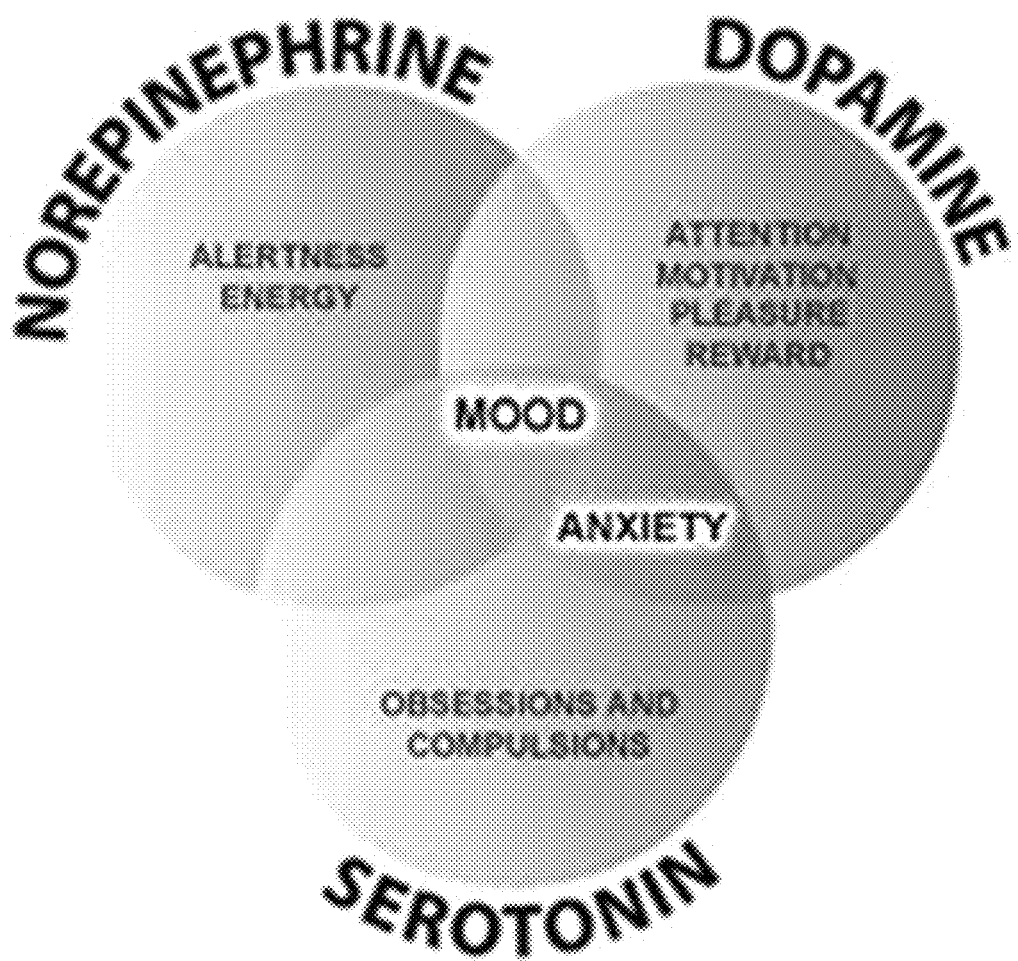
FIG. 1 is a Venn diagram providing neurotransmitter relationships of serotonin, norepinephrine, and dopamine as a result of the use of caffeine.

Caffeine achieves many of its effects by blocking the activity of adenosine, a neurotransmitter that affects almost every bodily system. Because one of the primary actions of adenosine is to activate drowsiness and sleep, caffeine, by blocking the uptake of adenosine, keeps us from feeling the effects of fatigue. As the Venn Diagram (FIG. 1) indicates, scientists have learned that, largely as a consequence of its blockade of adenosine receptors, caffeine also has profound effects on most of the other major neurotransmitters, including dopamine, acetylcholine, serotonin, and, in high doses, norepinephrine. By affecting these other neurotransmitters, caffeine is able to deliver energy in the form of thermogenesis to boost capacities even when humans are well-rested, something that could not be explained by the inhibition of adenosine alone. By increasing the transmission of dopamine, caffeine improves mood and there is evidence that it protects brain cells from age and disease related degeneration. By increasing the activity of acetylcholine, caffeine increases muscular activity. By serotonin levels, caffeine relieves depression and pro vides brain stimulation leading to relaxation, alertness and has even shown relief from migraine headaches. Though caffeine may lower serotonin levels, the synergistic effects of the formulation of this disclosure including β-phenylethylamine and hordenine mitigate or eliminate this caffeine-induced reduction of serotonin.

Studies have shown that caffeine binds to and inhibits adenosine receptors in the brain. Normally, when adenosine binds to these receptors, drowsiness occurs. Caffeine effectively prevents this response and instead allows for alertness. In addition, studies have shown that caffeine induces dopamine release in the brain thereby providing a synergistic effect with β-phenylethylamine. In addition, caffeine upregulates dopamine receptors in the brain.

Summarizing, caffeine, by acting to modifying and regulate a host of the body's neurotransmitters, enables humans to achieve enhanced capabilities in four major areas:

Cognitive:
Sharpens reasoning, memory, verbal fluency, concentration, and decision-making and heightens sensuous perception.

Affective:
Enhances moods, increases relaxation, relieves boredom, boosts self-confidence.

Physical:
Improves speed, endurance, strength, and reaction time by increasing thermogenesis, associated with fat burning and metabolic rate.

Therapeutic:
Protects body cells and especially brain cells from some kinds of long-term damage and delivers many other specific therapeutic benefits including pain relief and protection from the pulmonary complications of smoking and the damage from strokes.

Common Side Effects for Caffeine

Figure 2:
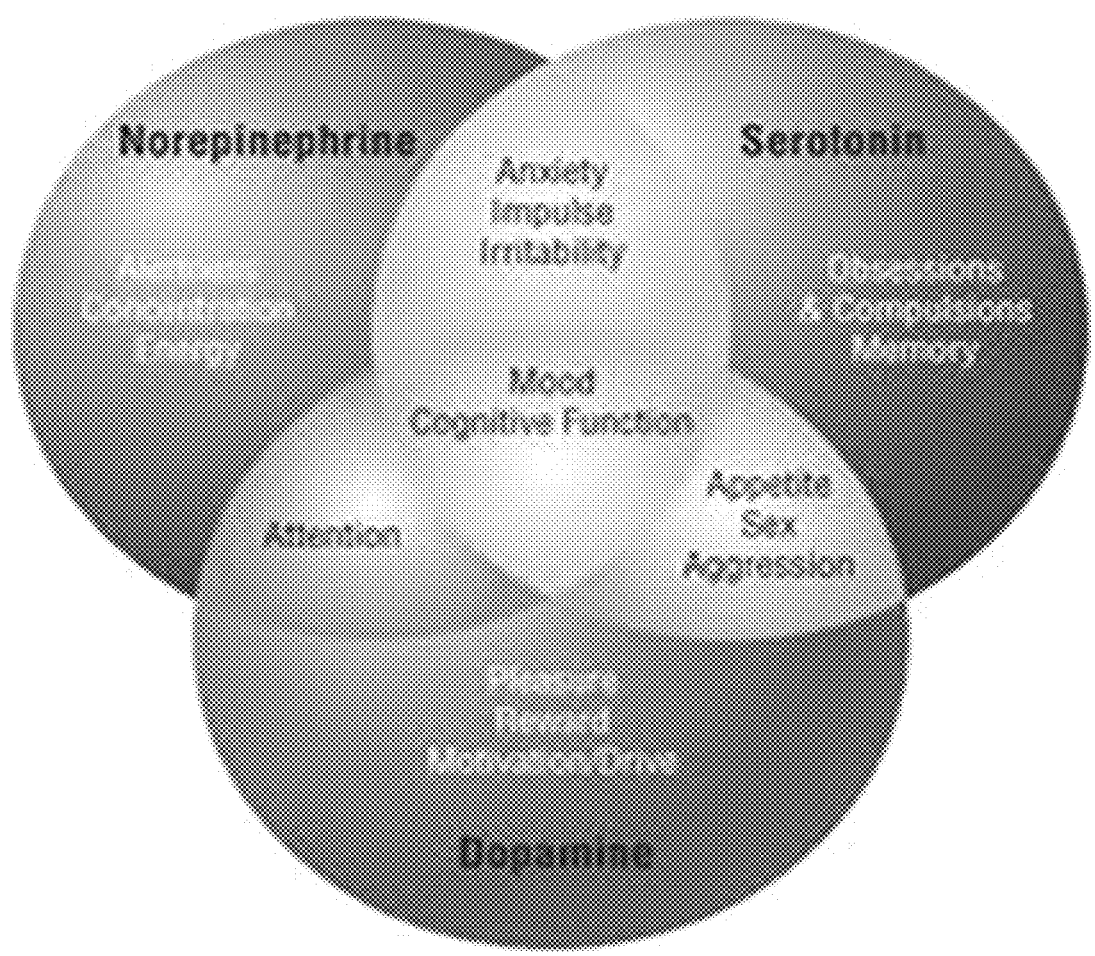
FIG. 2 is a Venn diagram providing a description of the known caffeine side effects.

As shown in the Caffeine Side Effects Venn Diagram (FIG. 2), the symptoms associated with withdrawal from caffeine can cause mild to clinically significant distress or impairment in daily functioning. Mild to increasingly severe physical dependence and withdrawal symptoms may occur upon abstinence, with greater than 100 mg caffeine per day. Some symptoms associated with psychological dependence may also occur during withdrawal. Caffeine dependence also is associated with withdrawal symptoms such as fatigue, headache, irritability, depressed mood, reduced contentedness, inability to concentrate, sleepiness or drowsiness, stomach pain, and joint pain. It has also been reported that withdrawal headaches are experienced by roughly half of those who stop consuming caffeine for two days following an average daily intake of 235 mg.

One of the problems with consuming caffeine in coffee is the sensation of withdrawal. When the body metabolizes caffeine, the initial effects of caffeine will resolve. Now with increased adenosine receptor expression without caffeine inhibition, a person may suffer fatigue and headaches from increased drowsiness and vasodilation induced by adenosine. Caffeine affects people differently. Some people can consume a moderate amount—about two 12-ounce cups of coffee—without experiencing adverse side effects, according to MedlinePlus.

Studies have shown that caffeine binds to and inhibits adenosine receptors in the brain. Normally, when adenosine binds these receptors, we feel drowsiness. Caffeine effectively prevents this response and, instead, we feel wakeful.

Figure 3:
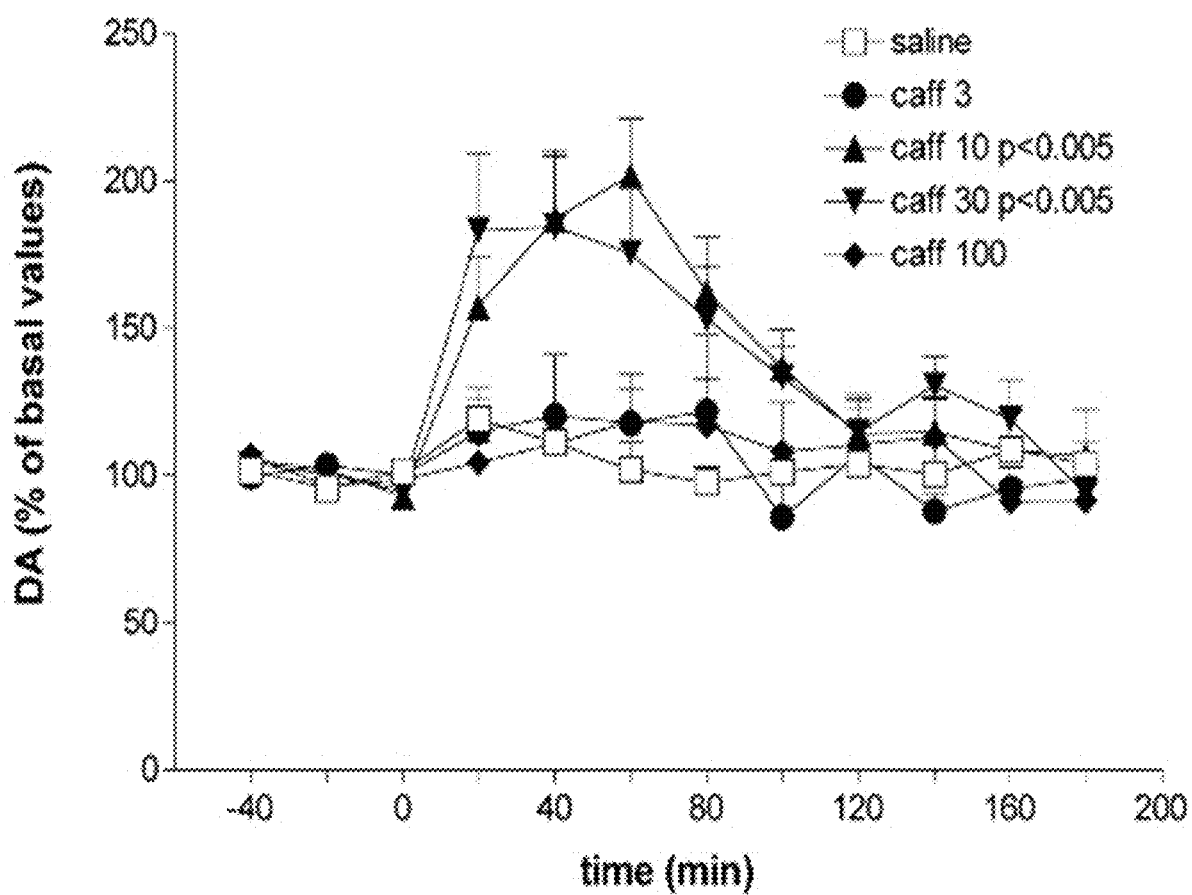
FIG. 3 is a plot indicating extracellular concentrations of dopamine (DA) in the shell of the NAc after intraperitoneal administration of saline or caffeine.

Aside from caffeine's effect with adenosine receptors, studies have shown that caffeine may induce dopamine release in the brain, thus having a synergistic effect with β-phenylethylamine. Additionally, it appears that caffeine upregulates dopamine receptors in the brain. FIG. 3 provides data to this effect.

β-phenylethylamine

Phenethylamine (PEA), also known as β-phenylethylamine (β-PEA) or 2-phenylethylamine is an organic compound and a natural monoamine alkaloid, a trace amine, and also the name of a class of chemicals with many members that are well known for their psychoactive and stimulant effects.

The known chemical structure (1) is shown below;

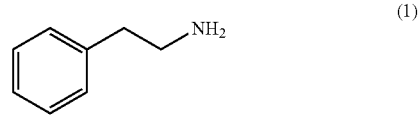

(1)

β-phenylethylamine functions as a monoaminergic neuromodulator or "mesencephalic enhancer" and, to a lesser extent, a neurotransmitter in the human central nervous system. It plays a key role in the functioning of our innate and acquired drives. There are enhancer-sensitive neurons in the brain that work in a split second on a high activity level due to the use of β-PEA. In mere microseconds, β-PEA causes an impulse-mediated release of catecholamines (dopamine and epinephrine) and serotonin in the brain. This causes rapidly occurring improvements in cognitive performance, attention, awareness, pleasure, libido, and it provides a sense of wellbeing. According to the pioneering research of Dr. Joseph Knoll, a respected neurochemist, pharmacologist, and emeritus professor, catecholamine levels (neurotransmitters such as dopamine and norepinephrine) reach maximum levels at sexual maturity in humans and then begin a long, gradual reduction. The rate of decline at least in part determines how rapidly a person ages. According to Dr. Knoll, catecholamine levels, learning ability, sexual activity, and longevity are all interlinked. It has been postulated that the efficiency of catecholamine brain machinery plays a major role in determining quality and duration of human life. Higher-performing, longer-living individuals have a more active, more slowly deteriorating catecholamine system than their lower-performing, shorter-living peers.

The boost of energy-generating catecholamines (dopamine and norepinephrine) produces amphetamine-like stimulation and performance enhancement. β-PEA is potent in promoting the efflux of catecholamines and blocking their re-uptake, especially that of dopamine. β-PEA also decreases the reuptake of serotonin albeit less efficiently. That means that β-PEA is a strong NDRI (Norepinephrine-Dopamine Reuptake Inhibitor) and a weaker-acting SSRI (Selective Serotonin Reuptake Inhibitor). Their synergistic actions make β-PEA an ideal nutraceutical complement or alternative to standard protocols and is one purpose of incorporating the use of hordenine, as further described below.

It has also been recognized that β-PEA's ability to elevate blood catecholamine levels may be useful in the thermogenic burning of stored body fat for losing weight. Increased levels of epinephrine and norepinephrine can stimulate beta-adrenergic receptors located on adipose (fat) tissue to release fatty acids into circulation as a fuel source. In other words, β-PEA, as with caffeine, can be used to increase the metabolism and further burn fat for energy. In addition, catecholamines act on hormone-sensitive lipase, the enzyme for removing fat from storage sites.

Starting around age twenty-five, there is a lifelong decline in catecholamine neurotransmitters (epinephrine, norepinephrine, and dopamine), a slower decline in the indoleamine neurotransmitter (serotonin), and a shifting imbalance of the catecholamine/serotonin ratio. Catecholamine deficiencies and neurotransmitter imbalances are a principal cause of loss of "hypothalamic sensitivity" for the progressive metabolic shifts that produce aging and the diseases of aging, according to Dr. Vladimir Dilman's *Neuroendocrine Theory of Aging*. β-PEA induces behavioral and physiological effects similar to those of amphetamine. Unlike amphetamine and other stimulants, researchers have referred to β-PEA as an "endogenous amphetamine" because the brain produces it. After ingesting β-PEA humans commonly report a surge of energy, wakefulness, alertness, attention and heightened senses.

According to Dr. Dilman, a renowned Russian bio gerontologist, aging is caused by a progressive loss of sensitivity by the hypothalamus (and related structures in the brain) to feedback inhibition from hormones and neurotransmitters. Throughout one's lifespan, this loss of sensitivity produces a progressive shifting away from internal balance and altered levels of hormones, neurotransmitters, and cell signalers. These are the cause of many post-maturational diseases, accelerated aging, and earlier death. The *Neuroendocrine Theory of Aging* explains in detail how this causes the major diseases of aging, which contribute to over 85 percent of early deaths of middle-aged and elderly individuals.

To correct catecholamine deficiencies to help delay aging, prolong life span, prevent aging disorders, and restore youthful biological functions, Dr. Dilman and other researchers in the field of anti-aging have suggested the following:

1. Increase neurotransmitter production and activity;
2. Decrease catecholamine breakdown from MAO-B enzymes;
3. Correct neurotransmitter deficiency and imbalance of the catecholamine/serotonin ratio;
4. Inhibit neurotransmitter re-uptake, to increase intersynaptic neurotransmitter levels
5. Correct the decrease in receptor sensitivity and responsiveness of target cells and tissues to neurotransmissions.

Current research on β-PEA trace amine receptor neuromodulator and neurotransmitter actions is reaping clinical rewards. β-PEA is proving beneficial for attenuating attention-related problems, controlling addictions, overcoming substance abuse, and correcting neurobehavioral problems. The success rate for treating depression with β-PEA has been shown to be equivalent to the effective percentage for the major Serotonin-Selective Re-uptake Inhibitors (SSRI's)—but without their serious side effects and toxicity. In fact, β-PEA has produced sustained relief of both acute and chronic depression in a significant number of people, including some who were unresponsive to standard protocols, according to research psycho-pharmacologist and psychiatrist Dr. Hector Sabelli. These are ongoing and exciting areas of research for ρ-PEA with many practical uses and clinical implications.

β-PEA is biosynthesized from the amino acid L-phenylalanine by enzymatic decarboxylation via the enzyme aromatic L-amino acid decarboxylase. In addition to its presence in mammals, β-phenethylamine is found in many other organisms and foods, such as chocolate, cauliflower, kale cabbage and acacia, especially after microbial fermentation. It is sold as a dietary supplement for purported mood and weight loss-related therapeutic benefits; however, orally ingested phenethylamine experiences extensive first-pass metabolism by monoamine oxidase B (MAO-B) and then aldehyde dehydrogenase (ALDH), which metabolize it into phenylacetic acid. This prevents significant concentrations from reaching the brain when taken in low doses.

As an endogenous stimulant of the human (and other mammals) brain, β-PEA amplifies the activity of major neurotransmitters thereby providing increased longevity, slower aging, higher performance, a sense of well-being, and a renewed youthful-functioning body. β-PEA increases the actions of dopamine (for well-being and feeling pleasure), norepinephrine (the brain's stimulant for wakefulness and higher performance), acetylcholine (for improving memory and mental activity), and serotonin (for better mood emotion and impulse control). β-PEA is a highly-concentrated neurotransmitter in the limbic system (the brain's emotional center) that increases motivation, physical drive, feelings, and social activity.

β-PEA is the parent compound of 1-deprenyl, a catecholamine-enhancing, dopamine-increasing, and neuroprotective compound with proven life extension actions in animal research. L-deprenyl produces a concentration spike in brain β-PEA. β-PEA releases acetylcholine, a neurotransmitter that plays an integral role in learning and memory. Brain receptors respond to acetylcholine by facilitating memory and higher cognitive functions. In addition, β-PEA increases noradrenaline action and causes release of the catecholamines which includes dopamine and epinephrine (adrenaline) required for alertness and concentration. It has also been shown that an increase in glutamate from β-PEA is involved with brain circuitry that helps form the neural networks associated with memories.

How β-PEA Functions in the Brain and Body β-PEA readily crosses the blood-brain barrier. It is rapidly available in the brain to increase neurotransmission by blocking neurotransmitter (catecholamines and indoleamine) reuptake, as a regulator of neurotransmitter transport and efflux, and an excitatory (stimulating) neurotransmitter in different region of the brain.

Amplifies Neurotransmitter Activity

β-PEA is released from nerve vesicles in the brain, causing an efflux of neurotransmitters in response to a given nerve signal, therefore providing amplification of nerve cell activity. β-PEA induces higher concentration, continuous robust efflux, and greater availability of dopamine (for feeling pleasure and wellbeing), norepinephrine (the brain's stimulant creating energy for movement), acetylcholine (for memory and cognitive functions), and serotonin (mood enhancement, and impulse control).

Modulates Neurotransmitter Functions by Binding TAAR1

β-PEA modulates neuro-transporter functions by binding with its paired Trace Amine-Associated Receptor 1 (TAAR1). TAAR1 is a G-protein coupled receptor that is activated by β-PEA and certain monoamines. Activation of TAAR1 by β-PEA significantly inhibits the uptake and induces efflux of the neurotransmitters dopamine, norepinephrine, and serotonin. β-PEA increases the extracellular levels of these neurotransmitters by inhibiting their reuptake into the pre-synaptic cell, and this increases their ability to provide beneficial activity throughout the body. Trace amines, including β-phenylethylamine (β-PEA), tyramine, tryptamine, and octopamine, have been known to be heterogeneously distributed in mammalian brain tissues, and their distribution spatially parallels the origins and terminal projection areas of the monoaminergic neurons. In monoaminergic neurotransmission, common biogenic amines, including dopamine, norepinephrine, and serotonin, are well established as neurotransmitters, which are synthesized from their precursor amino acids in neurons, stored in vesicles of neuronal terminals and released into the synaptic clefts to interact with both presynaptic and postsynaptic receptors. Although trace amines share similarities with common biogenic amines in structure, metabolism, and distribution, their roles and functional profiles in the brain are far from being as clear as those for common biogenic amines.

With high turnover rates, trace amines are dynamically regulated by enzymes and are present in the brain at generally low concentrations. No trace amine specific neurons have been discovered and were once thought of as metabolites or faux neurotransmitters. However, the rate in synthesis of trace amines is equivalent to that of dopamine and norepinephrine, and altered levels of the trace amines are associated with various neuropsychiatric disorders, which are hallmarked by changes in monoaminergic activity. These properties and amphetamine-like effects of the trace amines suggest that trace amines may serve as neuromodulators in the brain.

It has been confirmed that TAAR1 is widely expressed in the rhesus monkey brain (mammalian model), notably in monoaminergic nuclei and that rhesus monkey TAAR1 responds to a wide spectrum of chemicals, including trace amines. However, the functional interaction of TAAR1 with trace amines and the role that TAAR1 plays in the brain remain unclear. Previous data showed that TAAR1 signaling is enhanced by monoamine transporters and that TAAR1 activation can modulate DAT kinetics in vitro. Data collected by several investigators also showed co-localization of TAAR1 and DAT in a subset of dopamine neurons in the rhesus monkey and mouse substantia nigra. It was also observed that TAAR1 expression in norepinephrine transporter (NET)-positive neurons in the locus coeruleus of the rhesus monkey A 2008 study by Lindemann et al. (2008) reported TAAR1 expression in the dorsal raphe nucleus. These findings suggest that TAAR1 may serve as a presynaptic regulator in functional modulation of monoamine transporters. With respect to monoamine autoreceptors, it has been reported that their activation by monoamine neurotransmitters provides feedback regulation of monoamine neurotransmitter release but it is unknown whether trace amines exert any effects via monoamine autoreceptors. In a more recent study, the interaction of trace amines with TAAR1 and monoamine autoreceptors were investigated together with whether monoamine autoreceptors influence TAAR1 signaling and monoamine transporter function in response to trace amines. This study used transfected HEK293 cells and brain synaptosomes derived from nonhuman primates, wild-type mice, and TAAR1 knockout mice to investigate the effects of β-PEA activation of TAAR1 on the uptake and efflux function of DAT, NET, and serotonin transporter (SERT). The data confirm that all the trace amines tested recognize and excite TAAR1 and reveal that trace amines do not interact with monoamine autoreceptors to alter TAAR1 activity. The data also revealed that β-PEA alters monoamine transporter function via interacting with TAAR1 but not monoamine autoreceptors, which may suggest a common mechanism by which trace amines exert a modulatory role on monoamine transporters in the brain.

Homeostatic Regulator Guarding Against Metabolic Dysfunctions

β-PEA is also a neural guardian of homeostasis (maintaining healthy metabolic equilibrium). The binding of β-PEA with TAAR1 protects delicate neural circuitry against harmful changes. β-PEA self-regulates transmitter activity to prevent over-excitation or under-stimulation transmitter signal strength and activity. β-PEA acts as a homeostatic controller to maintain the neuronal activity within defined physiological limits to prevent metabolic dysfunctions and neurological disorders. This makes β-PEA and other trace amines perfect candidates for the development of novel therapeutics for a wide range of human disorders.

Endogenous Amphetamine-Like Stimulating Neurotransmitters

β-PEA is an excitatory neurotransmitter with its own receptor and a chemical structure similar to amphetamines that induces behavioral and electrophysiological effects similar to those of amphetamine. Ever, as mentioned above, unlike amphetamine, β-PEA is endogenous to the brain and does not develop tolerance or dependency, or produce any side effects, such as amphetamines sold under the trade name Adderall® and the adverse effects of the popular drug stimulant Ritalin® that is prescribed for treating Attention Deficit Disorders.

β-PEA may trigger neurotransmitters for "brain plasticity" and "neurogenesis" (the forming of new brain cells, information processing connections, and functions) that increase cognition, learning, memory, skills, smartness, and performance. The mechanism is thought to involve β-PEA's action of increasing dopamine neurotransmitters from synapses and acting as a dopamine re-uptake inhibitor in certain brain regions.

In summary, β-PEA has been found to act as a neurotransmitter by;
Preventing the reuptake and promoting efflux of dopamine which enhances pleasure, libido and emotional wellbeing.
Increasing epinephrine and norepinephrine catecholamine at nerve terminals, for energy production and inhibition of their re-uptake.
Increasing the action of acetylcholine (Decreasing the reuptake of acetylcholine) for cognitive functions by stimulating the AMPA glutamatergic receptors.
Elevating mental alertness and mood by suppressing the inhibitory effects of GABA-B receptors.
Preventing the reuptake and promoting efflux of serotonin which causes uplifting activity on mood, emotions, and control.

Furthermore, β-PEA regulates neurotransmitter activity to prevent aberrant neurosignaling. Thus β-PEA acts as a homeostatic regulator to maintain the neuronal activity of monoamine neurotransmitters within defined physiological limits.

Convincing evidence has been presented for using β-PEA in the treatment for a wide range of neurological dysfunctions and behavioral disorders, such as:
Affective disorders (depression)
Attention deficit/hyperactivity disorder
Cognitive dysfunction (brain fog, confusion, forgetfulness, poor concentration, a sluggish cognitive tempo, slowed reaction time, and diminished awareness)
Drug abuse and substance dependence (alcoholism, nicotine dependence, and addictions to methamphetamines, cocaine opioids, and psycho-stimulants)

Addictive behavior (gambling, sexual addiction)
Eating disorders (obesity, anorexia)

The human brain forms β-PEA from the essential amino acid 1-phenylalanine by an enzyme-driven cellular process. Phenylalanine is the precursor to the amino acid tyrosine, which produces the neurotransmitters dopamine, norepinephrine, and adrenaline in a sequential process, but phenylalanine supplements don't significantly boost β-PEA concentrations. It has been found that phenylalanine supplements can boost catecholamine neurotransmitter levels excessively, producing undesirable side effects including anxiety, headaches, and hypertension. In some cases phenylalanine has been shown to transform into neurotoxic (brain-damaging) metabolites. By contrast, β-PEA safely increases and amplifies the activity of dopamine, norepinephrine, and other brain transmitters to produce desirable and remarkable effects.

As also mentioned above, the human body can synthesize significant quantities of β-PEA, however, functional concentrations of β-PEA remain low due to its rapid metabolism via MAO-β (monoamine oxidase B). As result, β-PEA effects are not sustained. The beverage formulations of the present disclosure have been designed through a synergistic combination to increase the half-life of β-PEA allowing for sustainable effects.

Common Side Effects for β-PEA

Unlike drug stimulants that are highly addictive and harmful to your health, β-PEA produces non-toxic and non-addictive stimulation with limited side effects. β-PEA protects neurons and does not overstimulate the nervous system. β-PEA doesn't deplete neurotransmitter levels, it modulates them. This avoids the "crashing upon cessation of use" that is common with stimulant drugs. In terms of safety, β-PEA does produce the adverse effects of pharmaceutical NDRI's and SSRI's. This is due to β-PEA modulation of neurotransmissions and its intrinsic neuro-protective properties.

β-PEA does not involve habituation and produces limited side effects. β-PEA has been referred to by scientists as an "endogenous amphetamine" because it is produced naturally by the brain. Following ingestion of β-PEA people commonly report a surge of energy, wakefulness, alertness, and heightened senses. Because β-PEA is endogenous to the brain it seems to be a safer alternative to amphetamines sold under the trade name Adderall® and the adverse effects of the popular drug stimulant Ritalin® that are prescribed for treating Attention Deficit Disorders.

A single side effect which could be deleterious to health is that β-PEA has demonstrated appetite-reducing activity, reducing food intake in animal research.

In summary, β-phenylethylamine (β-PEA) is a trace monoamine produced endogenously (naturally) in the brain. It is synthesized from the modification of phenylalanine (amino acid) just like the neurotransmitters dopamine epinephrine, and norepinephrine (serotonin is synthesized from tryptophan). Current research shows that PEA decreases the reuptake of dopamine, serotonin, and norepinephrine causing enhancement of mood, energy and focus.

In the presence of β-PEA, there is less dopamine reuptake (more dopamine at nerve synaptic cleft). The data in FIGS. 4 and 5 indicate this effect for Rhesus monkeys.

Figure 4:
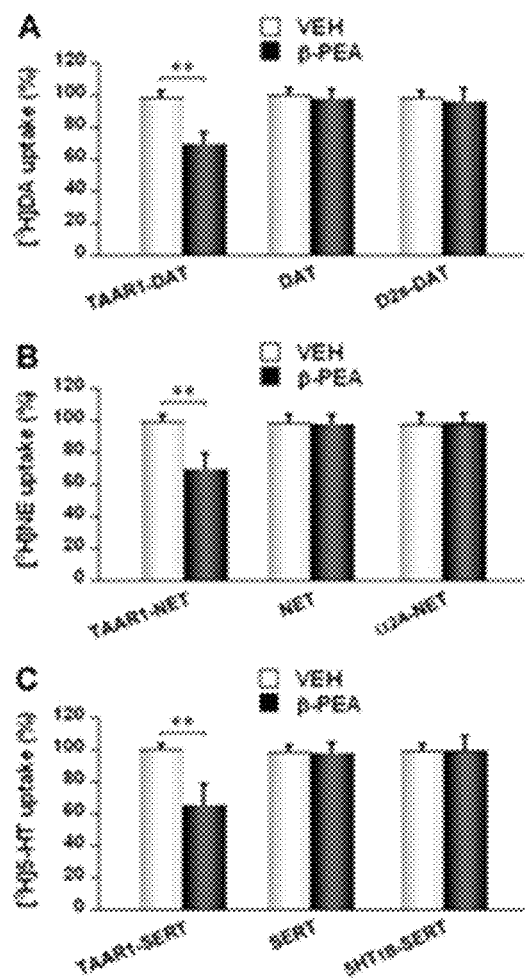
FIG. 4 is a plot indicating the influence of TAAR1 activation by β-PEA on the uptake function of the monoamine transporters in the cells.

FIG. 4 shows that β-phenylethylamine (β-PEA) does not directly interact with the monoamine transporters DAT (dopamine transporter), NET (norepinephrine transporter), or SERT (serotonin transporter). β-PEA does, however, does activate TAAR1, which subsequently modulates monoamine transporter function downstream. To demonstrate this, three cell lines were generated for each monoamine. For dopamine: a cell line expressing TAAR1 and DAT, a cell line expressing only DAT, and cell line expressing only D2s-DAT (a subtype of DAT) with the latter two being controls is shown. This was repeated for norepinephrine, serotonin and the respective transporters as well. Transporter activity with and without treatment with β-PEA was measured by determining the amount of tritium-labeled monoamine present inside the cells after treatment with stock solutions of the respective monoamines. The data indicates that β-PEA reduces the uptake of the monoamines by their respective transporters.

Figure 5:
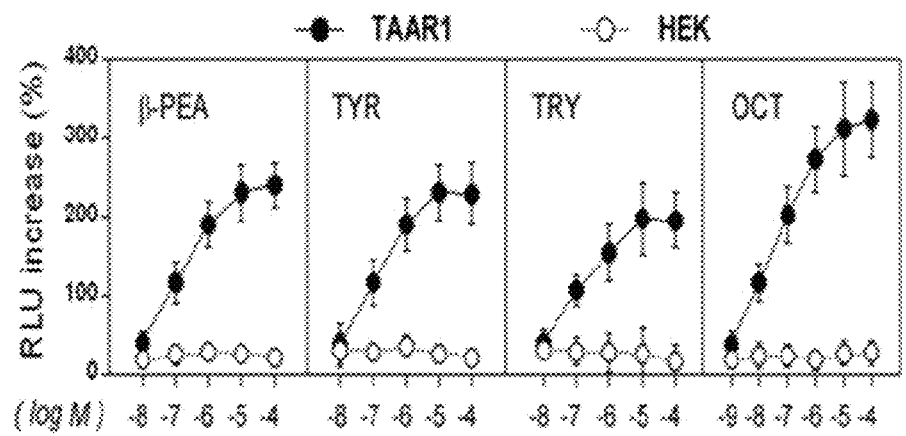
FIG. 5 is a plot indicating that the Trace Amine-Associated Receptor 1, TAAR1, is activated in the presence of the trace amines β-phenylethylamine (β-PEA), tyramine (TYR), tryptamine (TRY), and octopamine (OCT).

FIG. 5 shows that the Trace Amine-Associated Receptor 1, TAAR1, is activated in the presence of the trace amines β-phenylethylamine (β-PEA), tyramine (TYR), tryptamine (TRY), and octopamine (OCT). This activation results in an increase of cyclic adenosine monophosphate (cAMP) via activation of adenylyl cyclase. In order to determine this effect of the trace amines on TAAR1, HEK293 cells were transiently transfected with a rhesus monkey TAAR1 expression construct as well as CRE-Luc and pGL4.73 reporter systems to determine cAMP production. The data confirms β-PEA, TYR, TRY, and OCT activates TAAR1 whereas the control HEK cells did not produce cAMP.

Hordenine

Hordenine (N,N-dimethyltyramine) is an alkaloid of the phenethylamine class that occurs naturally in a variety of plants, taking its name from one of the most common, barley (*Hordeum* species). Chemically, hordenine is the N-methyl derivative of N-methyltyramine, and the N,N-dimethyl derivative of the well-known biogenic amine tyramine from which it is biosynthetically derived and with which it shares some pharmacological properties that are described below.

Hordenine is known as a stimulant of the central nervous system that causes a release of norepinephrine, and has the ability to promote weight loss by enhancing metabolism.

The known chemical structure (2) is shown below;

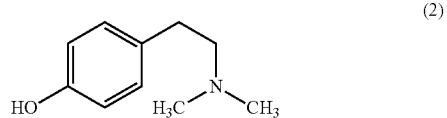

(2)

Hordenine is also a highly selective substrate of MAO-B and acts as a temporary reversible MAO-B inhibitor. Because hordenine crosses the blood-brain barrier it is able to inhibit MAO-B enzymes in both the body and brain. The method of action for β-PEA s different in that the human body can synthesize significant quantities of β-PEA, however, functional levels of β-PEA remain fairly low because it is usually broken down by the enzyme MAO-B within several hours. Hordenine is also antiasthmatic, antidiarrheal, antifeedant, antispasmodic, bronchorelaxant, cardiotonic, hepatoprotective, sympathicomimetic, and acts as a vasoconstrictor.

In comparison, caffeine can act as either a vasoconstrictor or vasodilator depending on dose and which areas of the body are being acted upon. This fact assists in providing synergies between β-PEA, hordenine and caffeine (another synergistic effect between caffeine and β-PEA is that caffeine seems to reduce serotonin levels whereas β-PEA decreases the reuptake-increasing serotonin at the nerve terminal).

The first report of the isolation from a natural source of the compound hordenine was made by Arthur Heffter in 1894, who extracted this alkaloid from the cactus *Anhalonium fissuratus* (now reclassified as *Ariocarpus fissuratus*), naming it "anhalin". Twelve years later, E. Léger independently isolated an alkaloid which he named hordenine from germinated barley (*Hordeum vulgare*) seeds. Ernst Späth subsequently showed that these alkaloids were identical and proposed the correct molecular structure for this substance, for which the name "hordenine" was ultimately retained.

Hordenine is present in a fairly wide range of plants, notably amongst the cacti, but has also been detected in some algae and fungi. It occurs in grasses, and is found at significantly high concentrations in the seedlings of cereals such as barley (*Hordeum vulgare*) (~0.2%, or 2000 μg/g), proso millet (*Panicum miliaceum*) (~0.2%), and sorghum (*Sorghum vulgare*) (~0.1%).[7] Reti, in his 1953 review of naturally-occurring phenethylamines, notes that the richest source of hordenine is the cactus *Trichocereus candicans* (now reclassified as *Echinopsis candicans*), which was found to contain 0.5-5% of the alkaloid.

It is known that hordenine is biosynthesized by the step-wise N-methylation of tyramine, which is first converted to N-methyltyramine, and which, in turn is methylated to hordenine. The first step in this sequence is accomplished by the enzyme tyramine N-methyltransferase (tyramine methylpherase), but it is uncertain if the same enzyme is responsible for the second methylation that actually produces hordenine.

It should be noted that the "methyl hordenine HCl" which is listed as an ingredient on the labels of some nutritional supplements is in all likelihood simply hordenine hydrochloride, since the description of "methyl hordenine HCl" given by virtually all bulk suppliers of this substance corresponds to that for hordenine hydrochloride (or possibly just hordenine). There are five regioisomeric compounds that would correspond to the name "methyl hordenine HCl", if it were interpreted according to the rules of chemical nomenclature: α-methyl hordenine, β-methyl hordenine, 2-methyl hordenine, 3-methyl hordenine, and 4-O-methyl hordenine—each in the form of its HCl salt.

In a 1995 study, Hapke and Strathmann reported that in dogs and rats hordenine produced a positive inotropic effect on the heart (i.e. increased the strength of contraction), increased systolic and diastolic blood pressure, and increased the volume of peripheral blood flow. Movements of the gut were inhibited. Additional experiments on isolated tissue lead these investigators to conclude that hordenine was an indirectly acting adrenergic agent that produced its pharmacological effects by releasing stored norepinephrine (NE).

In a study of the effects of a large number of compounds on a rat trace amine receptor (rTAR1) expressed in HEK 293 cells, it was found that hordenine, at a concentration of 1 μM, had almost identical potency to that of the same concentration of β-phenethylamine in stimulating 3',5'-cyclic adenosine monophosphate (cAMP or cyclic AMP) production through the rTAR1. cAMP is a "second messenger" important for many biological processes including intracellular signal transduction in many organisms. The potency of tyramine in this receptor preparation was slightly higher than that of hordenine.

cAMP is a second messenger important in many biological processes. cAMP is a derivative of adenosine triphosphate (ATP) and used for intracellular signal transduction in many different organisms, conveying the cAMP-dependent pathway.

Common Side Effects for Hordenine

In experimental animals, given sufficiently large doses parenterally (i.e. by injection) of hordenine produced an increase in blood pressure, as well as other disturbances of the cardio-vascular, respiratory, and nervous systems.

Modern studies were carried out by Frank and co-workers, who reported that intravenous (IV) administration of 2 mg/kg of hordenine to horses produced substantial respiratory distress, increased the rate of respiration by 250%, doubled the heart rate, and caused sweating without changes in basal body temperature or behavior. All effects disappeared within 30 minutes. The same dose of hordenine given orally did not produce any of the effects seen after parenteral administration.

Combining Hordenine with other MAO inhibitors or pharmaceutical drugs for depression and anxiety is ill advised. Most of the following side effects only occur at much higher than recommended doses and include: nausea, insomnia, dizziness, anxiety, upset stomach, mood swings, rapid heart rate, and possibly hallucinations.

In summary, hordenine is a substrate of monoamine oxidase B (MAO-B). When taken with β-phenylethylamine (PEA), hordenine effectively prevents MAO-B from rapidly metabolizing β-PEA and dopamine. MAO-B inhibition increases the half-life of n-PEA and dopamine resulting in prolonged effect with no sudden crash.

Figure 6:
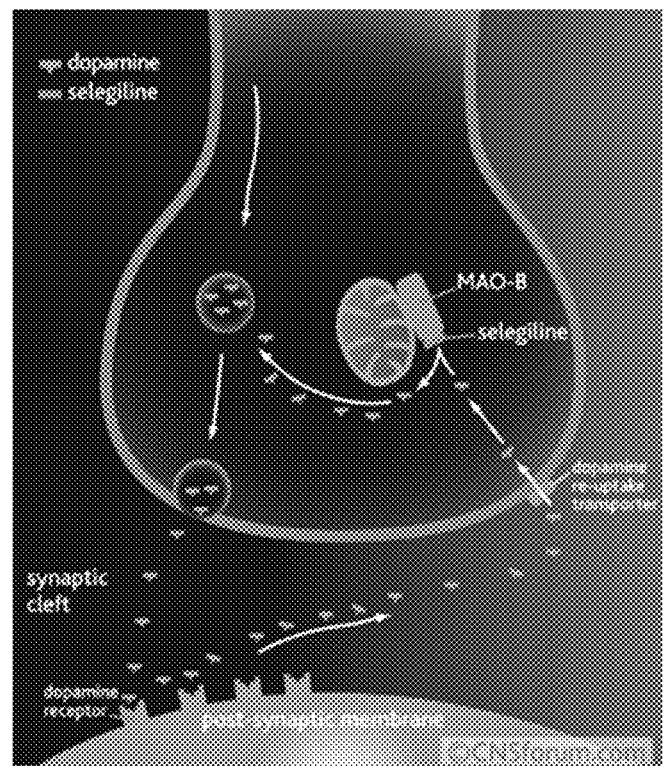
FIG. 6 is a schematic illustrating the competitive inhibition of MAO-B by hordenine.

FIG. 6 illustrates how the inhibition of MAO-B by hordenine prevents the rapid metabolism (increases half-life) of dopamine thereby subsequently allowing for accumulation of dopamine at the synaptic cleft that controls neuron transport to the brain as well as to other organs.

The B Vitamins and their Impact on Brain Function

The B-vitamins comprise a group of eight water-soluble vitamins that perform essential, closely inter-related roles in cellular functioning, acting as co-enzymes in a vast array of catabolic and anabolic enzymatic reactions. Their collective effects are particularly prevalent and associated with numerous aspects of brain function, including energy production (thermogenesis), DNA/RNA synthesis/repair, genomic and non-genomic methylation, and the synthesis of numerous neurochemicals and signaling molecules.

Human epidemiological and controlled trial investigations, and the resultant scientific commentary, have focused almost exclusively on the small sub-set of vitamins ($B_9/B_{12}/B_6$) that are the most prominent (hut not the exclusive) B-vitamins involved in homocysteine metabolism.

There has been a dearth of scientific studies involving the other B vitamins. Nonetheless, there is no doubt that evidence clearly indicates closely inter-related functions of the eight B-vitamins and suggesting that adequate levels of all members of this group of micronutrients are essential for optimal physiological and neurological functioning. Surprisingly, given their pivotal physiological significance, the role of the B group of vitamins thiamine ($B_1$), riboflavin ($B_2$), niacin ($B_3$), pantothenic acid ($B_5$), vitamin ($B_6$), folate ($B_9$) and vitamin ($B_{12}$) in health and brain function is limited in several respects. As an example, the major human epidemiological and controlled trial research effort in this area has concentrated almost exclusively on the small sub-set of B vitamins (folate, $B_9$, vitamin $B_{12}$ and, to a lesser extent vitamin $B_6$) that play the most obvious roles in homocysteine metabolism. The multifarious inter-related roles of the remaining five B vitamins ($B_1$, $B_2$, $B_3$, $B_5$ and $B_7$) have been largely overlooked.

Possibly as a result of this, the many intervention studies that have involved administering just folic acid ($B_9$), vitamins $B_{12}$ and/or $B_6$, have generated equivocal results. Similarly, while there is evidence that the minimum levels of each B vitamin required in order to prevent explicit deficiency related diseases is clear, we have a poor understanding of the negative effects of levels of consumption that lie above the minimum, but under the optimal level of consumption for these vitamins. Indeed, there is no clear idea of where the optimal level of consumption may lie. The inter-related cellular functions of the entire group of B vitamins in catabolic and anabolic metabolism is nonetheless well known.

Furthermore, evidence from human research clearly shows both that a significant proportion of the populations of developed countries suffer from deficiencies or insufficiencies in one or more of this group of vitamins, and that, in the absence of an optimal diet, administration of the entire B-vitamin group, rather than a small sub-set, at doses greatly in excess of the current governmental recommendations, would be a rational approach for preserving brain health.

Given that B vitamins are essential for every aspect of human brain function, and that large proportions of the population of developed societies have less than optimal levels of vitamins, it would be expected that a relationship would be evident between vitamin B consumption and mental function both in terms of epidemiological studies and controlled intervention trials. The impetus for much of the research conducted to date in both of these domains has been associated with the "homocysteine hypothesis". Concentrating on this one unproven hypothesis has resulted in both observational and controlled trial research being focused disproportionately on just three of the B vitamins—folate or folic acid $B_9$, $B_6$ and $B_{12}$. However, the observational and the controlled trial research concentrating on these three vitamins could be seen as generating somewhat different conclusions. To give an idea of the size of the epidemiological research effort in this area, a review paper published in 2008 by Smith summarized the relevant research published in the previous 10 years. It described, irrespective of quality for over 34,000 subjects that no correlation was found for 90% of the studies involving brain function and the use of the three (3) B vitamins, folate ($B_9$), $B_6$, and $B_{12}$ It was particularly noteworthy that less than 10% of the studies incorporated in the review included an assessment of vitamin $B_6$, and no studies investigated the relationships pertaining to any of the remaining five B vitamins. Since Smith's paper, a number of meta-analyses of data from the more methodologically rigorous, recently published studies have been conducted, although it is notable that these analyses applied differing methodological inclusion criteria, and almost exclusively included studies involving samples of elderly adults. These meta-analyses show a reasonably clear relationship between homocysteine levels and dementia in cross-sectional and prospective studies, with high serum homocysteine at the study outset associated with a 35% increased chance of subsequently developing dementia across eight studies and a 50% greater chance of suffering clinically significant cognitive decline across a further 14 studies. Interestingly, at the other end of the life-span, a single study also demonstrated a positive relationship between dietary folate intake and academic achievement in adolescents.

Each of these meta-analyses included differing collections of studies, depending on their investigational aims and inclusion/exclusion criteria, and this factor may be all important in dictating the eventual results. As an example, Lopez da Silva et al. in a comprehensive review encompassing the relationship between a number of micronutrients and dementia, noted that 14 out of 31 studies that they identified that had assessed folate, and only nine out of 33 studies that had assessed vitamin $B_{12}$ actually demonstrated decreased vitamin levels in sufferers from Alzheimer's disease. However, no studies reported the opposite relationship, and meta-analysis of the overall data confirmed the relationships. This study was interesting in two further respects. The first was that it included a meta-analysis of data from studies in which the dementia and control populations had equivalent nutrition, ruling out the confounding effects of any disease related differences in overall diet on the results. The second was that it also illustrated the extreme bias in observational studies towards investigations involving folate and Vitamin $B_{12}$. In contrast to this voluminous body of work, only two studies included an investigation of either thiamine or vitamin $B_6$, and no studies assessed the relationships between levels of the other B vitamins and any aspect of brain function.

Thiamine ($B_1$), Riboflavin ($B_2$), Niacin ($B_3$), Pantothenic Acid ($B_5$), and Biotin ($B_7$)

Unfortunately, there is a general dearth of controlled trial research regarding the effects of the remaining B vitamins on brain function, or indeed any aspect of functioning in humans. Some supportive evidence does exist that shows that several of this group can modulate peripheral cardiovascular and gluco-regulatory function—and it is certainly the case that modulation of these parameters would have an impact on brain function. A single study has assessed the direct effects of 50 mg (i.e., 40 times the Recommended Dietary Allowance (RDA) or 40 RDA) of thiamine ($B_1$) or placebo administered for two months to 120 young females with adequate thiamine ($B_1$) status at the study outset. The results showed that thiamine improved mood as assessed by the Profile of Mood States, and improved attention as evinced by faster decision times in two-choice, four-choice and eight-choice reaction time tasks.

There is clear evidence that the cellular functions of B vitamins are closely inter-related, but no definitive research to date has attempted to elucidate the effects of the full range of B vitamins with regard to any aspect of brain function (or indeed any other function). However, a growing body of research has assessed the effects of multi-vitamins/minerals which include a full range of B vitamins. The comparative contributions of the B vitamins in these treatments cannot ultimately be differentiated from those of the other vitamins and minerals in the interventions, these treatments could certainly be conceived as providing a clearer picture of the effects of "B vitamins" as a group than the research that has focused on folic acid, often with additional vitamin $B_{12}$ and sometimes with vitamin $B_6$. This research can typically also be differentiated from that summarized above on the basis that it has typically employed samples of cognitively intact, children and non-elderly adults.

Interestingly, the orthodoxy that vitamins have to be administered for an extended period of time in order to elicit any physiological effects is not based on evidence that vitamins cannot exert acute effects. Comparatively few studies have assessed the acute effects of vitamins, but from those studies that have, there is emerging evidence that vitamins have physiological and brain function effects following a single dose. For instance, single doses of a range of single vitamins, including folic acid (as well as vitamins C, E, A), administered at "mega-doses" of between five and 26 times the RDA for that micronutrient, have all been shown to increase vasodilation in groups with disease-related or experimentally induced endothelial dysfunction. Acute administration of vitamin $B_6$ has also been shown to elicit increased serotonin synthesis in the primate brain, while, in a placebo controlled, double blind, cross-over study in humans, the higher of two single doses of vitamin $B_6$ (100 mg, 250 mg) also engendered an increase in dream salience (vividness, bizarreness, emotionality, and color). A recent study at the University of Maryland confirms that vitamin $B_6$ is implicated in the synthesis of serotonin in the body.

The direct acute effects of single doses of multi-vitamins (plus minerals) on brain function have also been assessed in several studies. Haskell et al. investigated the effects of a multivitamin/mineral on cognitive function in children after a single dose (and after four and eight weeks) and found that improvements in attention task performance and in a semantic memory task were evident as early as 3 h following the first dose. Two studies have also demonstrated that a single dose of a multi-vitamin/mineral can significantly modulate regional brain activity during a task measuring focused attention as measured with functional magnetic resonance spectroscopy (fMRI), and cerebro-electrical activity during an attention task as measured by electroencephalography (EEG).

In the latter study EEG changes following the multi-vitamin treatment correlated with changes in task performance. A recent study also investigated the impact of two doses of multi-vitamins/minerals that differed on the basis of their water soluble vitamin content (1 RDA and 3 RDA—recommended daily allowance) on cerebral blood-flow in the frontal cortex (using Near Infrared Spectroscopy) and overall energy expenditure and metabolism (using Indirect calorimetry of exhaled gas) during difficult cognitive tasks. This study demonstrated significantly increased fat metabolism and overall energy expenditure during cognitive task performance within 2 h of consuming the higher dose (3 RDA) of water soluble vitamins, and increased cerebral blood-flow following the lower 1 RDA dose of vitamins.

Regarding supplementation with multi-vitamins, Benton, reviewed the results of studies published within the preceding decade that had assessed the effects of supplementation with multi-vitamin/minerals on children's intelligence (IQ). All of the treatments included a full range of B vitamins, typically administered at much higher levels than the adult RDA. Benton noted evidence of improved performance in 10 out of the 13 studies, with improvements exclusively restricted to non-verbal tests of intelligence (i.e., those "fluid" intelligence tasks that do not require knowledge or vocabulary and which could therefore be conceived as more closely reflecting the biological functioning of the brain). Eilander et al. revisited the subject with a meta-analysis that included 15 multivitamin mineral studies, 12 of which had involved administration of a full range of B vitamins, with a further two of the remainder including folate ($B_9$) and vitamins $B_{12}$ and $B_6$ alongside other vitamins.

They concluded that there was evidence of a "marginal increase in fluid intelligence and academic performance in healthy schoolchildren". Similarly, Frensham et al. reviewed those studies from developed countries that included effect sizes and identified 10 studies that showed cognitive benefits, as opposed to four that did not. They concluded that these results show that multivitamin supplementation may engender benefits in nonverbal intelligence and in other behavioral measures.

For adults, Kennedy and Haskell identified 10 studies involving chronic multi-vitamin supplementation, almost exclusively conducted in cohorts of non-elderly adults. In these 10 studies, all but one study reported improved psychological/cognitive functioning following supplementation. In a subsequent meta-analysis of some of the cognitive data from 10 controlled trials of multi-vitamins that employed several similar memory measures, Grima et al. found that multi-vitamin supplementation improved performance of some memory tasks, with too little data on tasks assessing other cognitive domains to arrive at a conclusion. A subsequent meta-analysis of the data from eight studies that included an assessment of the effects of multivitamins on aspects of mood and psychological state found that supplementation reduced clinical ratings of perceived stress, mild psychiatric symptoms and anxiety.

Of particular interest, the studies included in this analysis could be subdivided into those that administered higher (4 RDA) levels of B vitamins with lower levels of other micronutrients, or lower (1 RDA) levels of B vitamins with higher levels of other micronutrients. This analysis suggested that higher B vitamins with lower levels of other micronutrients engendered stronger effects, suggesting both a dose-response and that the efficacy of the products lay primarily with the B vitamin constituents.

These conclusions received further support from a more recent study that also demonstrated improved mood following four weeks of supplementation with a multivitamin containing high levels of B vitamins. Interestingly, several of the studies included in the reviews described above also included assessments of homocysteine levels before and after treatment, and demonstrated both that homocysteine levels were approaching levels indicating cardiovascular risk in the studies' healthy, non-elderly samples, and also that multivitamins normalized these levels including in a dose-related manner when 1 RDA and 3 RDA of B vitamins were administered.

It is also worth noting that a number of other recent studies have also demonstrated improved psychological or cognitive functioning following products containing multi-vitamins, although the interpretation of these studies with regards their vitamin content is limited by the inclusion of multiple herbal extracts at potentially psychoactive levels in the formulations. However, it may be relevant that one of these studies demonstrated a correlation between improved performance in a focused attention (Stroop) task and changes in blood levels of vitamin $B_6$ following supplementation.

In summary, the B vitamins represent a group of eight essential dietary micronutrients that work closely in concert at a cellular level and which are absolutely essential for every aspect of brain function. As water soluble nutrients, they are generally safe at levels of consumption well in excess of the recommended minimum consumption levels (possibly with the exception of folic acid).

While adequate levels of all of the B vitamins should be obtainable from a healthy diet, evidence suggests that large sub-sections of the populations of developed countries are suffering deficiencies or marginal deficiencies in one or more B vitamins that will predispose them to a number of negative health consequences, including less than optimal brain function.

Both epidemiological and controlled intervention trial research, driven by the predominant "homocysteine hypothesis", have overly concentrated on the relationships with brain function, and the effects of supplementation on brain function of a narrow group of three homocysteine lowering B vitamins—folate ($B_9$) and vitamin $B_{12}$ and, to a lesser extent, vitamin $B_6$. As described above, the potential roles and effects on brain function of the remaining five inter-related B vitamins have been largely ignored. As a consequence, consistent evidence suggests that biochemical levels of this narrow band of three vitamins, and related levels of the amino-acid homocysteine, correlate positively and negatively with brain function, respectively.

However, the evidence that supplementation with one or more of these three homocysteine lowering vitamins in isolation improves brain function is entirely equivocal. Certainly, the smaller body of research investigating multivitamins, which has largely been undertaken in healthy children and non-elderly adults, suggests significant benefits to brain function following supplementation with multivitamin products containing a full range of B vitamins at levels well in excess of their RDAs.

It is also notable that treatments containing all of the B vitamins will inevitably reduce homocysteine and indeed, given the direct contribution of both niacin and riboflavin to the folate/methionine cycles, they should theoretically be more effective than small sub-groups of B vitamins in this regard. For the moment, the foregoing suggests that research should, at a minimum, be redirected towards elucidating the potential benefits for brain function of both the acute and chronic administration of a full range of B vitamins rather than concentrating solely on the chronic effects of a small sub-group of three of the B vitamins.

There is some evidence that the combination of 1-(aminomethyl)cyclohexaneacetic acid)—known as gabapentin—an amine based substance similar in chemical structure to the trace amines with oral administration of B vitamins increases the antiallodynic effect of gabapentin in the rat. Results indicate that systemic administration of gabapentin and B vitamins can interact synergistically to reduce neuropathic pain in the rat and suggest the use of this combination to relieve neuropathy in humans. The dosage and type of B vitamins in the study was 100:100:1 of vitamin $B_1$, $B_6$ and $B_{12}$, respectively. Peripheral neuropathy describes damage to the peripheral nervous system, which transmits information from the brain and spinal cord to every other part of the body. Impaired function and symptoms depend on the type of nerves—motor, sensory, or autonomic—that are damaged. As described above and pointed out in this study, the use of the B vitamins $B_6$ and $B_{12}$ in the present formulations may be responsible for assisting with neurotransmission relieving any painful symptoms either induced or existing for those consuming the beverages.

Side Effects for B Vitamins

Side effects of taking a B vitamin complex are not common. Taking excessive amounts of a vitamin B complex can cause side effects. An overdose is signaled by: dizziness, frequent urination, change in the color of the urine, black stools, constipation, diarrhea, abdominal pain. nausea, vomiting, redness of the skin and itching.

In severe cases, patients may develop an allergic reaction to administering an oral dosage of vitamin B complexes. Symptoms include itching, rashes, kidney stones, swelling, wheezing or hives. Patients may also experience side effects from excessive exposure to a specific B vitamin. For the vitamins used in the present beverage formulations, more specific information is given below;

Vitamin $B_3$—Niacin

Niacin will frequently cause flushing, which may include burning, sweating, tingling, redness or chills. These can last as long as 4 hours after taking the supplement, but this is a harmless condition. Other common side effects of taking niacin include upset stomach, nausea, vomiting. diarrhea, heartburn or dizziness. In severe cases, taking niacin can result in persistent headache, irregular heartbeat, swelling of the arms or legs, joint pain, or blurred vision. In rare cases patients may also experience intense abdominal pain, incessant nausea or vomiting, bloody or black stools, yellowing of the eyes and muscle or joint pain. Allergic reactions to niacin can result in swelling of the lips, tongue, throat or face, itching or hives.

Vitamin $B_5$—Pantothenic Acid

Patients who take pantothenic acid are very prone to overdose. This can result in severe diarrhea. In rare cases, patients may develop an allergic reaction which may result in tightness of the chest, trouble breathing or swelling of the face, throat, lips or tongue.

Vitamin $B_6$—Pyridoxine

Effects of pyridoxine include stomach pain, drowsiness, tingling, and loss of appetite, nausea, or vomiting. Frequently ingesting large doses of pyridoxine can cause brain and nerve problems. In rare cases, this can lead to a numbing sensation in various parts of the body, most notably in the hands and feet, poor coordination or extreme fatigue. Allergic reactions to pyridoxine can result in swelling of the face, tongue, lips or throat, trouble breathing or hives.

Vitamin $B_9$—Folic Acid

Taking excessive amounts of folic acid can increase the risk of heart attack, particularly in those who already suffer from heart trouble. Overusing folic acid may also increase your risk of developing lung or prostate cancer. Those receiving injections of folic acid may experience pain and swelling or pain near the injection site. In severe cases allergic reactions may cause, swelling of the lips, face or tongue, tightness in the chest, hives, rash or dizziness.

Vitamin $B_{12}$—Cyanocobalamin

Patients using cyanocobalamin may experience diarrhea, itching or an increased risk of blood clots. In severe cases, allergic reactions to cyanocobalamin can cause chest pain, swelling of the face, tongue, or lips, swelling of the body, muscle weakness, fever, chills, bruising or bleeding.

Summarizing, collectively, B-vitamins and micronutrients are essential for numerous aspects of brain function and normal physiological functioning including energy production, DNA/RNA synthesis/repair, genomic and non-genomic methylation, the synthesis of numerous neurochemicals and signaling molecules. Since these organic compounds are not produced endogenously, it is important to obtain them through diet. One important nutrient included in the energy drinks of this disclosure is biotin (vitamin $B_7$). Biotin plays a key role in glucose metabolism (energy) and haemostasis, including regulation of hepatic glucose uptake, gluconeogenesis, insulin receptor transcription and pancreatic β-cell function. Lower circulating levels of biotin have been reported for those suffering from Type II diabetes. To circumvent these effects from insufficient nutrition, the energy drinks of the present disclosure can often be formulated with the essential micronutrients and B-vitamins niacin (niacinamide), vitamin $B_6$ (pyridoxine hydrochloride), folate (folic acid), vitamin $B_{12}$ (cyanocobalamin), vitamin $B_7$ (biotin), and vitamin $B_5$ (pantothenic acid) in order to sustain important physiological functions pertaining to cognition and energy.

The nutraceutical beverage formulations of the present disclosure combines the scientific understanding of the synergistic effects described in detail above by including at least the three basic components of caffeine, phenylethylamine (β-PEA), and hordenine with water. Optional addition of the B vitamins assists with supporting brain function as described in detail above. These thermogenesis enhancing components provide a consumable product that reduces and in some cases eliminates the sudden "crash" (aka withdrawal symptoms described above) often experienced with leading energy drink brands. The synergistic effect of the ingredients delivers the burst of energy (thermogenesis), increased mental concentration and stamina needed to accomplish daily goals, tasks, and elevate overall human performance.

The composition selected has been carefully with the proper concentrations to provide the optimal dose for maximum effect with minimal side effects to ensure slowing of metabolic uptake and reduction to ensure that there will be little or no residual drowsiness or de-energization.

One such composition is for a 12 ounce "energy blend" beverage formulation wherein 12 ounces of this beverage would comprise water together with the following components;

a). 297 mg phenylethylamine citrate
b). 150 mg phenylethylamine HCl
c). 150 mg caffeine (synthetic)
d). 30 mg hordenine HCl
e). 20 mg green coffee bean extract collectively within a sufficient amount of properly treated water so that these miscible substances create a 12 ounce beverage. The water is normally carbonated water. The water can be provided from a distilled source, a natural spring, a deionization unit, or even a municipal drinking source that is filtered to remove contaminants. The water can be buffered to provide a selected pH either before, during after carbonation. The carbonated water can be obtained from a natural spring or the water can be intentionally carbonated by diffusing $CO_2$ through the water.

Representative pharmaceutically acceptable calcium salts include calcium chloride, calcium tartrate, calcium maleate, calcium lactate, calcium citrate, calcium phosphate, calcium acetate, calcium carbonate, calcium hydrogen carbonate, calcium lactate calcium fumarate, calcium sulfate, calcium bromide, calcium mesylate, calcium palmoate, calcium iodide, calcium nitrate, calcium gluconate and calcium methylsulfate. Alternatively, sodium and magnesium salts of these types may be equally acceptable.

During the course of developing these beverage formulations, it is often desirable to add a type of sugar and/or a sugar substitute that is a food additive that provides a sweet taste like that of sugar while containing significantly less food energy. Some sugar substitutes are produced by nature, and others produced synthetically.

An exhaustive list of the possible use of sugars and sugar substitutes is impossible, but at least includes and is not limited to caloric sugars including; sucrose, mannose, dextrose, all forms of fructose including crystalline fructose, high fructose (such as corn derived syrups), monk fruit sugars, glucose syrup, honey, Fruit Juice Concentrates, maltodextrin, trehalose, and *stevia*. A further listing is provided below;

Artificial Sweeteners
  Saccharin
  Aspartame
  Acesulfame-K
  Sucralose
  Neotame
Sugar Alcohols/Polyols
  Sorbitol
  Mannitol
  Xylitol
  Erythritol
  D-Tagatose
  Isomalt (Palatinat)
  Lacititol
  Maltitol
  HSH Hydrogenated Starch Hydroslsates, Maltito
  Glycerol
  Polydextrose Artifical Sweeteners, Not Yet Approved by FDA
  Alitame
  Cyclamates
  Neohesperdine
  Thaumatin With respect to ultimate dosing preferences, concentration levels within these beverage formulations are developed based on typical human subjects (e.g. a 70 kg subject). If the present composition is used in other mammals or in various human subjects, it may be necessary to modify the dosage. Modification of dosages based on the needs of the subject is well within the skill of the ordinary artisan. It is therefore understood that these dosage ranges are by way of example only, and that daily administration can be adjusted depending on various factors. The specific dosage of the compounds to be administered, and the duration of treatment are interdependent. The dosage and treatment regimen will also depend upon such factors as the specific components used, the efficacy of the components and the specific attributes required for each of the possible combinations of beverages that can be produced. Compliance with government regulations including packaging and labeling issues provide additional requirements that must be considered in order to properly commercialize these beverages.

One such requirement involves the understanding and demands associated with shelf life for these beverage formulations. A technique used to determine if the use of an aluminum can (which would be used for example to hold 8-16 ounces of one of the beverage formulations of the present disclosure) is known as "cyclic polarization". This technique involves a sample of aluminum body stock that is immersed in the beverage to be tested and utilizes aluminum electrode potentials determine corrosivity levels associated with each beverage. To control corrosion resistance of the cans, one method utilized has been to control the (normally as produced) pH of the beverage. In one embodiment, this required use of β-phenylethylamine citrate which created a pH of 2.64 for the orange and 2.79 for the berry flavored beverages respectively.

In creating these beverages with these respective pH values it was possible to utilize the highest rated internal epoxy can coating provided by Ball Corporation—BPA NI—(bis-phenol A non-intent) epoxy coating that is designed to reduces or eliminates the possibility of BPA contamination (a known toxic substance with known endocrine disrupting properties).

FIG. 7A and FIG. 7B depict a standard operating procedure (SOP) for making beverages of the present disclosure is included below;

1.1.1. The purpose of this procedure is to outline the process for preparing a small batch of Energy Drinks known as beverage formulations in this specification.
2. Scope
  2.1.1. This procedure applies to all personnel trained to perform research and develop these formulations.

In addition to the SOP provided above, there are many additional methods of making specific beverage formulations. Examples 1-3 below indicate several possible compositions for making these beverages. The first two pertain to 12 ounce beverages normally contained in aluminum cans. These beverage formulations could also be contained and provided in appropriate glass and/or plastic containers with and without liners.

FIG. 8 depicts an energy beverage formulation of the present disclosure.

FIG. 9 depicts another example of the components of a beverage formulation of the present disclosure.

FIG. 10 depicts a third example of the components of a beverage formulation of the present disclosure.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

We claim:

1. A nutraceutical beverage formulation providing enhanced thermogenesis, mental concentration, and stamina to mammals, comprising a caffeine with a concentration between 0.0001 grams to 0.3 grams, a β-phenylethylamine with a concentration between 0.00001 grams to 1 gram, a hordenine with a concentration of 0.00001 grams to 0.1 grams, and water, wherein the formulation contains only ingredients capable of crossing the blood-brain barrier.

2. The beverage formulation of claim 1, wherein said hordenine is a salt of hordenine.

3. The beverage formulation of claim 1, wherein said β-phenylethylamine is β-phenylethylamine citrate.

4. The beverage formulation of claim 1, wherein said β-phenylethylamine comprises a salt of β-phenylethylamine.

5. The beverage formulation of claim 1, wherein the caffeine, the β-phenylethylamine, and the hordenine act synergistically to increase catecholamine and indoleamine concentrations and wherein synergism is accomplished as the caffeine, β-phenylethylamine, and hordenine in a blood stream cross a blood-brain barrier within a brain of a consumer after consumption of said formulation, thereby reducing or eliminating acute symptoms associated with rapid decline of said catecholamine and indoleamine concentrations in said blood stream.

6. The beverage formulation of claim 5, wherein the caffeine, the β-phenylethylamine, and the hordenine undergo a metabolic breakdown resulting in a controlled decrease in said catecholamine and indoleamine concentrations in said blood stream such that said concentrations revert to a pre-existing basal level.

7. The beverage formulation of claim 1, wherein the β-phenylethylamine decreases serotonin reuptake, the hordenine prevents metabolic breakdown of β-phenylethylamine and maintains serotonin levels, while the caffeine decreases serotonin levels.

8. The beverage formulation of claim 1, wherein the β-phenylethylamine diminishes reduction of serotonin levels that occur following prolonged consumption of the caffeine.

9. The beverage formulation of claim 1, further comprising a B vitamin.

10. The beverage formulation of claim 9, wherein said B vitamins provide additional cognitive enhancing attributes including mental clarity, concentration and stamina.

11. The beverage formulation of claim 1, further comprising a B vitamin complex, said B vitamin complex including $B_3$, $B_5$, $B_6$, $B_7$, $B_9$, and $B_{12}$ mixed together in any combination and in a concentration that will further reduce or eliminate side effects associated with any of the caffeine, the β-phenylethylamine, or the hordenine and said vitamin B complex within said beverage formulations during or after human consumption.

12. The beverage formulation of claim 1, further comprising a sweetener including sugars and/or sugar substitutes.

13. The beverage formulation of claim 12, wherein said sugars are selected from the group consisting of: sucrose, crystalline fructose, high fructose syrups, mannose, dextrose, monk fruit sugar, maple syrup, and honey.

14. The beverage formulation of claim 12, wherein said sugar substitutes are selected from the group consisting of: stevia, saccharin, aspartame and sucralose.

15. The beverage formulation of claim 14, wherein said stevia is an earth grown derived form of stevia.

16. The beverage formulation of claim 1, wherein said formulations include an addition of flavors.

17. The beverage formulation of claim 16, wherein said flavors are natural flavors.

18. The beverage formulation of claim 16, wherein said flavors are organic flavors.

19. The beverage formulation of claim 1, wherein the caffeine is a green coffee bean extract.

20. The beverage formulation of claim 1, comprising a buffered water which is pH adjusted with buffering agents to either increase or decrease pH of said distilled, deionized, and/or filtered water.

21. The beverage formulation of claim 1, further comprising a pharmaceutical grade salt selected from the group consisting of: calcium salts, magnesium salts, and sodium salts.

22. The beverage formulation of claim 21, wherein said acceptable salts enhance flavor and efficacy of said formulation specific to improving mental clarity, concentration, and both physical and mental stamina.

23. The beverage formulation of claim 1, wherein said water is carbonated water.

24. The beverage formulation of claim 1, wherein said water is non-carbonated water.

25. A nutraceutical beverage formulation providing enhanced thermogenesis, mental concentration, and stamina to mammals, comprising a caffeine with the concentration between 0.0001 grams to 0.3 grams, a β-phenylethylamine with the concentration between 0.00001 grams to 0.1 grams, and a hordenine with the concentration between 0.0001 grams to 1 grams, wherein a boost of energy-generating catecholamines from said caffeine including dopamine and norepinephrine produces amphetamine-like stimulation and performance enhancement and wherein the β-phenylethylamine further promotes an efflux of said catecholamines that blocks re-uptake of said catecholamines and simultaneously decreases reuptake of serotonin and the formulation contains only ingredients capable of crossing the blood-brain barrier.

26. The beverage formulation of claim 25, wherein said uptake of said catecholamines is predominantly that of dopamine.

27. The beverage formulation of claim 26, wherein the hordenine stabilizes said β-phenylethylamine by reducing metabolic breakdown of the β-phenylethylamine during and after consumption.

28. The beverage formulation of claim 27, wherein the β-phenylethylamine acts as a strong NDRI (Norepinephrine-Dopamine Reuptake Inhibitor) and a much weaker-acting SSRI (Selective Serotonin Reuptake Inhibitor).

29. The beverage formulation of claim 25, wherein a synergistic action of the β-phenylethylamine with the hordenine and the caffeine provide prolonged mental and physical benefits and diminish or eliminate unwanted withdrawal symptoms after consumption by reduction of adrenaline and dopamine perturbations.

30. The beverage formulation of claim 29, said synergistic action of the β-phenylethylamine with the hordenine and the caffeine provide prolonged mental and physical benefits and diminish or eliminate unwanted withdrawal symptoms after consumption by elimination of adrenaline and dopamine perturbations.

31. A method of making a nutraceutical beverage formulation for increasing thermogenesis, said method comprising a caffeine with the concentration between 0.0001 grams to 0.3 grams, a β-phenylethylamine with the concentration between 0.00001 grams to 0.1 grams, and a hordenine with the concentration between 0.00001 grams to 1 grams, together with water, said components provided by adding to a container each of said components in selected amounts providing selected concentration(s) and mixing said components into water, thereby creating solubility of said components in a solution, thereby forming a basis for said formulation, wherein the formulation contains only ingredients capable of crossing the blood-brain barrier.

32. The method of claim 31, wherein to said solution, additional components including sugar, sugar substitutes, B vitamins, colorants, flavorings, thickening agents, stabilizers, and preservatives can be added thereby achieving a final beverage formulation for mammalian consumption.

33. The method of claim 32, wherein said final beverage formulation improve functional conditions in mammals associated with mental clarity, concentration, and stamina.

34. The method of claim 31, wherein consumption of said nutraceutical beverage formulation includes an administration route selected from the group consisting of oral buccal, sublingual, and combinations thereof.

35. The method of claim 31 wherein said beverage formulation is in a liquid beverage form utilizing carbonated water.

36. The method of claim 31 wherein said beverage formulation is in a liquid beverage form utilizing non-carbonated water.

* * * * *